US012208231B2

(12) United States Patent
Wine et al.

(10) Patent No.: US 12,208,231 B2
(45) Date of Patent: Jan. 28, 2025

(54) FLUID CONNECTOR SYSTEM

(71) Applicant: CareFusion 303, Inc., San Diego, CA (US)

(72) Inventors: Jason Andrew Wine, Brea, CA (US); David Stockey, Holly Springs, NC (US); Leah Paige Gaffney, Orange, CA (US); Siddarth K. Shevgoor, Mission Viejo, CA (US)

(73) Assignee: CareFusion 303, Inc., San Diego, CA (US)

( * ) Notice: Subject to any disclaimer, the term of this patent is extended or adjusted under 35 U.S.C. 154(b) by 96 days.

(21) Appl. No.: 18/089,310

(22) Filed: Dec. 27, 2022

(65) Prior Publication Data
US 2023/0139756 A1     May 4, 2023

Related U.S. Application Data

(63) Continuation-in-part of application No. 17/853,811, filed on Jun. 29, 2022.
(Continued)

(51) Int. Cl.
*A61M 39/26*     (2006.01)
*A61M 39/10*     (2006.01)
*A61M 39/24*     (2006.01)

(52) U.S. Cl.
CPC ............ *A61M 39/26* (2013.01); *A61M 39/10* (2013.01); *A61M 2039/1027* (2013.01);
(Continued)

(58) Field of Classification Search
CPC ............ A61M 39/26; A61M 2039/267; A61M 2039/268; A61M 2039/2426;
(Continued)

(56) References Cited

U.S. PATENT DOCUMENTS 5,713,856 A      2/1998  Eggers et al.
5,807,348 A  *   9/1998  Zinger ............... A61M 39/045
                                                      604/537
(Continued)

FOREIGN PATENT DOCUMENTS

EP     1678070 A2     7/2006
EP     1517723 B1     1/2007
(Continued)

OTHER PUBLICATIONS

International Search Report and Written Opinion for Application No. PCT/US2023/037112, dated Feb. 14, 2024, 11 pages.
(Continued)

*Primary Examiner* — David Colon-Morales
(74) *Attorney, Agent, or Firm* — Morgan, Lewis & Bockius LLP

(57) ABSTRACT

Fluid connector systems including first and second valve assemblies couplable together to form a fluid pathway therethrough, and can resist fluid flow through the connector system when the valve assemblies are separated from each other, the first valve assembly including a post forming a fluid passage, and the second valve assembly including a valve plug positioned within a bore and configured to obstruct a fluid passage, such that when the valve assemblies are separated, a slit of the valve plug resist fluid flow therethrough, and when the valve assemblies are coupled together the post extends through the compressible valve and engagement of a ridge of the valve plug against the post resist fluid flow between the post and the ridge.

19 Claims, 9 Drawing Sheets

Related U.S. Application Data

(60) Provisional application No. 63/217,165, filed on Jun. 30, 2021.

(52) U.S. Cl.
CPC ..... *A61M 2039/1061* (2013.01); *A61M 39/24* (2013.01); *A61M 2039/2426* (2013.01); *A61M 2039/267* (2013.01)

(58) Field of Classification Search
CPC .......... A61M 39/24; A61M 2039/1027; A61M 39/10; A61M 39/045; A61M 2039/1061
See application file for complete search history.

(56) References Cited

U.S. PATENT DOCUMENTS

| | | | | |
|---|---|---|---|---|
| 5,814,024 | A * | 9/1998 | Thompson | A61M 39/045 604/86 |
| 5,820,614 | A * | 10/1998 | Erskine | F16L 55/1007 604/905 |
| 6,706,022 | B1 * | 3/2004 | Leinsing | A61M 39/26 604/247 |
| 6,802,490 | B2 * | 10/2004 | Leinsing | A61M 39/26 604/905 |
| 6,808,161 | B1 * | 10/2004 | Hishikawa | F16L 29/005 604/167.04 |
| 6,874,522 | B2 | 4/2005 | Anderson et al. | |
| 7,004,934 | B2 * | 2/2006 | Vaillancourt | A61M 39/26 604/533 |
| 7,040,598 | B2 * | 5/2006 | Raybuck | A61M 39/26 251/149.1 |
| 7,153,296 | B2 | 12/2006 | Mitchell | |
| 7,350,764 | B2 | 4/2008 | Raybuck | |
| 7,396,051 | B2 | 7/2008 | Baldwin et al. | |
| 7,763,013 | B2 | 7/2010 | Baldwin et al. | |
| 7,766,394 | B2 | 8/2010 | Sage et al. | |
| 7,794,675 | B2 | 9/2010 | Lynn | |
| 7,803,139 | B2 | 9/2010 | Fangrow, Jr. | |
| 7,803,140 | B2 | 9/2010 | Fangrow, Jr. | |
| 7,815,614 | B2 | 10/2010 | Fangrow, Jr. | |
| 7,841,581 | B2 * | 11/2010 | Thorne, Jr. | A61M 39/26 251/149.6 |
| 7,857,285 | B2 * | 12/2010 | Lee | F16K 1/12 251/149.6 |
| 7,914,502 | B2 * | 3/2011 | Newton | A61M 39/045 604/246 |
| 7,918,243 | B2 | 4/2011 | Diodati et al. | |
| 7,998,134 | B2 | 8/2011 | Fangrow et al. | |
| 8,123,738 | B2 | 2/2012 | Vaillancourt | |
| 8,133,209 | B2 * | 3/2012 | Guala | A61M 39/045 604/167.03 |
| 8,142,418 | B2 | 3/2012 | McMichael et al. | |
| 8,211,069 | B2 | 7/2012 | Fangrow, Jr. | |
| 8,262,628 | B2 | 9/2012 | Fangrow, Jr. | |
| 8,343,113 | B2 * | 1/2013 | Hokanson | A61M 39/045 604/256 |
| 8,361,408 | B2 | 1/2013 | Lynn | |
| 8,480,968 | B2 | 7/2013 | Lynn | |
| 8,777,908 | B2 | 7/2014 | Fangrow, Jr. | |
| 8,777,909 | B2 | 7/2014 | Fangrow, Jr. | |
| 8,795,256 | B1 | 8/2014 | Smith | |
| 8,888,758 | B2 | 11/2014 | Mansour | |
| 8,899,267 | B2 | 12/2014 | Diodati et al. | |
| 8,910,919 | B2 * | 12/2014 | Bonnal | A61M 39/1011 604/533 |
| 8,974,425 | B2 * | 3/2015 | Tachizaki | F16L 37/30 604/905 |
| 8,974,437 | B2 | 3/2015 | Williams et al. | |
| 9,114,242 | B2 | 8/2015 | Fangrow et al. | |
| 9,126,028 | B2 | 9/2015 | Fangrow et al. | |
| 9,126,029 | B2 | 9/2015 | Fangrow et al. | |
| 9,192,753 | B2 | 11/2015 | Lopez et al. | |
| 9,234,616 | B2 | 1/2016 | Carrez et al. | |
| 9,358,379 | B2 | 6/2016 | Fangrow, Jr. | |
| 9,433,769 | B2 | 9/2016 | Bayly | |
| 9,468,749 | B2 | 10/2016 | Mansour et al. | |
| 9,492,649 | B2 | 11/2016 | Carrez et al. | |
| 9,579,495 | B2 * | 2/2017 | Tachizaki | F16L 37/30 |
| 9,580,214 | B2 * | 2/2017 | Hatton | A61M 39/045 |
| 9,636,492 | B2 | 5/2017 | Fangrow, Jr. | |
| 9,724,504 | B2 | 8/2017 | Fangrow, Jr. et al. | |
| 9,724,505 | B2 | 8/2017 | Williams et al. | |
| 9,861,805 | B2 | 1/2018 | Dennis et al. | |
| 9,933,094 | B2 | 4/2018 | Fangrow | |
| 9,974,939 | B2 | 5/2018 | Fangrow, Jr. | |
| 9,974,940 | B2 | 5/2018 | Fangrow, Jr. | |
| 10,029,086 | B2 | 7/2018 | Nowak et al. | |
| 10,156,306 | B2 | 12/2018 | Fangrow | |
| 10,173,045 | B2 | 1/2019 | Mansour | |
| 10,179,203 | B1 | 1/2019 | Huslage et al. | |
| 10,179,231 | B2 * | 1/2019 | Nelson | A61M 39/26 |
| 10,315,025 | B2 | 6/2019 | Phillips et al. | |
| 10,398,887 | B2 | 9/2019 | Fangrow, Jr. et al. | |
| 10,441,507 | B2 | 10/2019 | Sanders | |
| 10,518,078 | B2 | 12/2019 | Stjernberg Bejhed et al. | |
| 10,569,073 | B2 | 2/2020 | Hallisey et al. | |
| 10,625,068 | B2 | 4/2020 | Leuthardt et al. | |
| 10,655,768 | B2 | 5/2020 | Jones et al. | |
| 10,697,570 | B2 | 6/2020 | Fangrow | |
| 10,744,315 | B2 * | 8/2020 | Sanders | A61J 1/2065 |
| 10,751,523 | B2 * | 8/2020 | Rogier | F16K 25/005 |
| 10,842,982 | B2 | 11/2020 | Fangrow, Jr. | |
| 10,857,346 | B2 | 12/2020 | Dennis et al. | |
| 10,864,362 | B2 | 12/2020 | Jones et al. | |
| 10,881,847 | B2 | 1/2021 | Lynn | |
| 10,918,851 | B2 * | 2/2021 | Guala | A61M 39/26 |
| 11,135,417 | B2 * | 10/2021 | Yoshioka | A61M 5/14 |
| 11,168,818 | B2 | 11/2021 | Fangrow | |
| 11,207,514 | B2 | 12/2021 | Kakinoki | |
| 11,235,135 | B2 | 2/2022 | Tsai | |
| 11,235,136 | B2 * | 2/2022 | Rogier | A61M 39/26 |
| 11,273,297 | B2 * | 3/2022 | Kakinoki | A61M 39/26 |
| 11,484,471 | B2 | 11/2022 | Sanders | |
| 11,491,084 | B2 * | 11/2022 | Ueda | A61M 39/14 |
| 2003/0209681 | A1 * | 11/2003 | Leinsing | A61M 39/26 604/905 |
| 2004/0215158 | A1 | 10/2004 | Anderson | |
| 2005/0090805 | A1 | 4/2005 | Shaw et al. | |
| 2006/0129109 | A1 | 6/2006 | Shaw et al. | |
| 2007/0066965 | A1 * | 3/2007 | Coambs | A61M 39/14 604/533 |
| 2007/0088292 | A1 | 4/2007 | Fangrow, Jr. | |
| 2007/0088293 | A1 | 4/2007 | Fangrow, Jr. | |
| 2007/0088294 | A1 | 4/2007 | Fangrow, Jr. | |
| 2007/0088324 | A1 | 4/2007 | Fangrow, Jr. | |
| 2007/0225635 | A1 | 9/2007 | Lynn | |
| 2008/0039803 | A1 | 2/2008 | Lynn | |
| 2011/0106046 | A1 | 5/2011 | Hiranuma | |
| 2014/0249487 | A1 | 9/2014 | Lynn | |
| 2014/0330254 | A1 | 11/2014 | Rosenberger et al. | |
| 2016/0000363 | A1 | 1/2016 | Jones et al. | |
| 2017/0080203 | A1 * | 3/2017 | Yeh | A61M 39/045 |
| 2018/0200147 | A1 | 7/2018 | Sanders | |
| 2019/0184152 | A1 | 6/2019 | Kakinoki | |
| 2019/0282797 | A1 | 9/2019 | Tsai | |
| 2020/0113784 | A1 | 4/2020 | Lopez et al. | |
| 2020/0179672 | A1 | 6/2020 | Kakinoki | |
| 2020/0215319 | A1 | 7/2020 | Fangrow, Jr. et al. | |
| 2020/0284385 | A1 | 9/2020 | Fangrow | |
| 2020/0323734 | A1 | 10/2020 | Ueda et al. | |
| 2020/0338331 | A1 | 10/2020 | Sanders | |
| 2021/0069484 | A1 | 3/2021 | Tsai | |
| 2021/0077803 | A1 | 3/2021 | Lynn | |
| 2021/0252267 | A1 | 8/2021 | Fangrow, Jr. | |
| 2021/0388926 | A1 | 12/2021 | Martin et al. | |
| 2021/0393938 | A1 | 12/2021 | Lynn et al. | |
| 2022/0260189 | A1 | 8/2022 | Deuse | |

(56) References Cited

U.S. PATENT DOCUMENTS

| | | |
|---|---|---|
| 2022/0282814 A1 | 9/2022 | Fangrow |
| 2023/0001172 A1 | 1/2023 | Wine et al. |

FOREIGN PATENT DOCUMENTS

| | | |
|---|---|---|
| EP | 1622675 B1 | 8/2009 |
| EP | 2144634 A1 | 1/2010 |
| EP | 2298407 A1 | 3/2011 |
| EP | 2694132 A1 | 2/2014 |
| EP | 2562456 B1 | 6/2014 |
| EP | 2782633 A1 | 10/2014 |
| EP | 1842002 B1 | 4/2015 |
| EP | 2736582 B1 | 5/2015 |
| EP | 2089094 B1 | 1/2016 |
| EP | 2219721 B1 | 12/2017 |
| EP | 2753396 B1 | 12/2017 |
| EP | 2736584 B1 | 4/2018 |
| EP | 3305361 A1 | 4/2018 |
| EP | 2271398 B1 | 11/2018 |
| EP | 2480281 B1 | 11/2018 |
| EP | 2790750 B1 | 11/2018 |
| EP | 2331191 B1 | 3/2019 |
| EP | 3079756 B1 | 3/2019 |
| EP | 2121114 B1 | 5/2019 |
| EP | 2719419 B1 | 5/2019 |
| EP | 2956204 B1 | 8/2019 |
| EP | 3421077 B1 | 8/2019 |
| EP | 3530313 A1 | 8/2019 |
| EP | 3538201 A1 | 9/2019 |
| EP | 3570807 A1 | 11/2019 |
| EP | 3570809 A1 | 11/2019 |
| EP | 2536463 B1 | 4/2020 |
| EP | 3381505 B1 | 5/2020 |
| EP | 3538201 B1 | 5/2020 |
| EP | 1904152 B1 | 12/2020 |
| EP | 2150307 B1 | 12/2020 |
| EP | 3313490 B1 | 1/2021 |
| EP | 3760275 A1 | 1/2021 |
| EP | 3851155 A1 | 7/2021 |
| EP | 3517164 B1 | 9/2021 |
| EP | 3954355 A1 | 2/2022 |
| EP | 3960229 A1 | 3/2022 |
| EP | 3973044 A1 | 3/2022 |
| EP | 3305361 B1 | 5/2022 |
| EP | 3134052 B1 | 8/2022 |
| EP | 3530313 B1 | 8/2022 |
| WO | WO-2021099437 A1 | 5/2021 |
| WO | WO-2021180675 A1 | 9/2021 |
| WO | WO-2021252197 A1 | 12/2021 |
| WO | WO-2022042956 A1 | 3/2022 |
| WO | WO-2022149339 A1 | 7/2022 |
| WO | WO-2022207560 A1 | 10/2022 |

OTHER PUBLICATIONS

International Search Report and Written Opinion for Application No. PCT/US2022/035344, dated Oct. 10, 2022, 16 pages.

Bangert, Bill, "Shorter times to blood transfusion associated with decreased death risk in trauma patients", Medical Xpress, Apr. 14, 2016, https://medicalxpress.com/news/2016-04-shorter-blood-transfusion-decreased-death.html.

Icumedical, "ChemoClave™ Needlefree Close System Transfer Device (CSTD)", date unknown, https://www.icumed.com/products/oncology/closed-system-transfer-devices/chemoclave.

Icumedical, "ChemoLock™ Needlefree Closed System Transfer Device (CSTD)", date unknown, https://www.icumed.com/products/oncology/closed-system-transfer-devices/chemolock.

IVteam, "Force-activated separation IV connectors", 2022, Retrieved from the internet https://www.ivteam.com/intravenous-literature/force-activated-separation-iv-connectors/ [Last retrieved Jan. 13, 2023].

Lineus Medical, SafeBreak Product Features and Benefits Brochure, May 2021, mkg 0058 May 2021 Rev. 02.

PRZen, "Lineus Medical Goes International, Signs ONEY for Distribution in Korea", PRZen Online Press Release Distribution, PrZen/33448014, MKG-0130 Rev 00, Retrieved from the internet https://przen.com/pr/lineus-medical-goes-international-signs-oney-for-distribution-in-korea-przen-33448014 [Last retrieved Jan. 13, 2023].

Rickard, et al., "Securing All intraVenous devices Effectively in hospitalised patients—the SAVE trial: study protocol for a multicentre randomised controlled trial", BMJ Open, Sep. 23, 2015;5(9):e008689, doi: 10.1136/bmjopen-2015-008689. PMID: 26399574; PMCID: PMC4593168.

Tada Group AB, LinkedIn Post "ReLink granted patent in Japan", LinkedIn, Mar. 2022, retrieved from the internet https://se.linkedin.com/company/tadamedical?trk=public_post_reshare_feed-actor-image&original_referer= [Last retrieved Mar. 2022].

Tribology, "Coefficient of friction, Rolling resistance and Aerodynamics", date unknown, https://www.tribology-abc.com/abc/cof.htm.

Written Opinion from the International Preliminary Examining Authority for Application No. PCT/US2023/037112, dated Aug. 22, 2024, 5 pages.

* cited by examiner

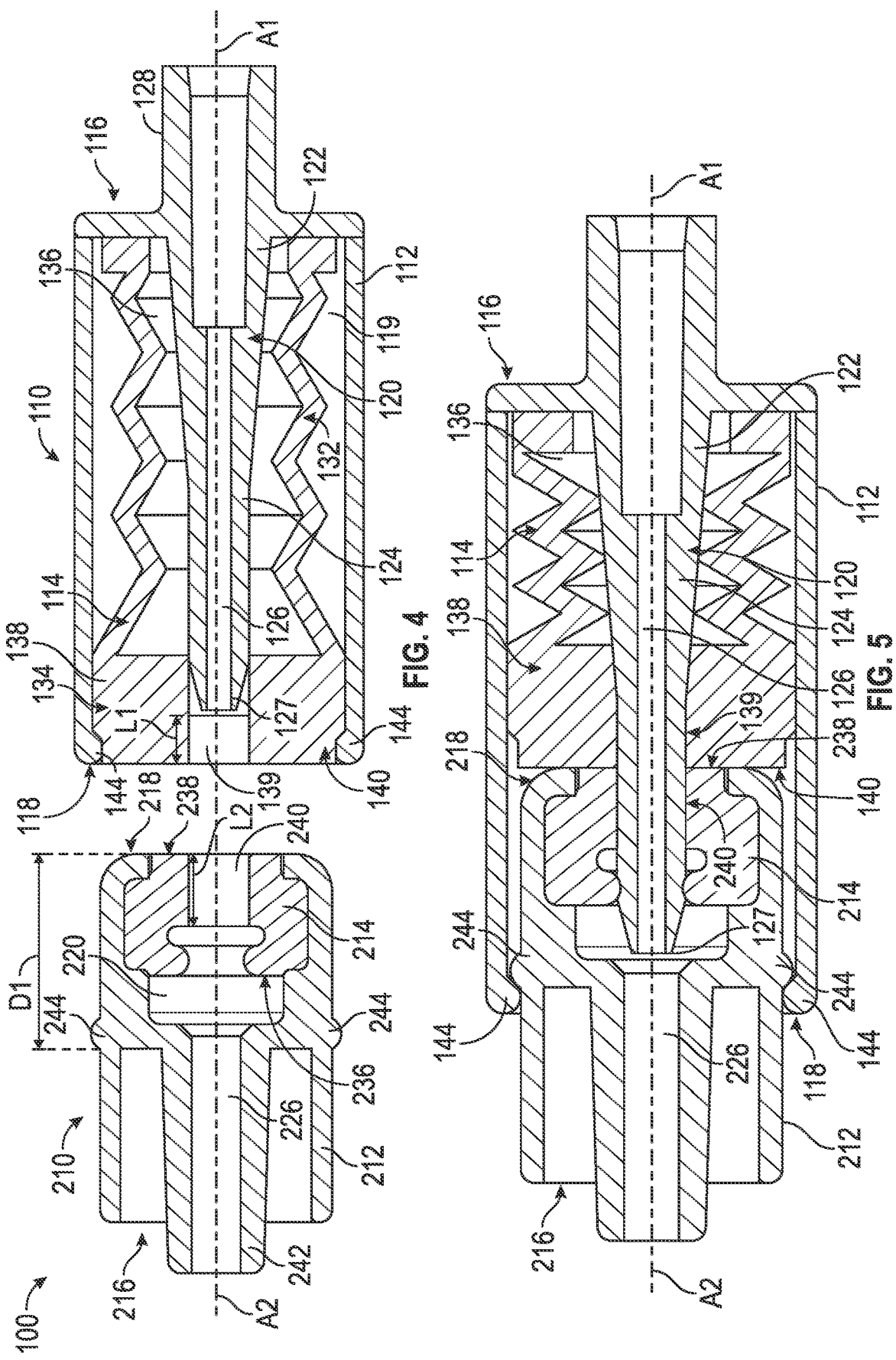

FLUID CONNECTOR SYSTEM

CROSS REFERENCE TO RELATED APPLICATIONS

This application is a continuation-in-part of U.S. patent application Ser. No. 17/853,811, filed on Jun. 29, 2022, which claims the benefit of U.S. Provisional Application No. 63/217,165, filed Jun. 30, 2021, the entire disclosure of each of these applications being incorporated herein in its entirely by this reference.

BACKGROUND

The present disclosure relates generally to medical fluid connectors and, more particularly, to fluid connector systems having valve assemblies that can be coupled together to form a fluid pathway.

Medical connections are widely used in fluid delivery systems such as those used in connection with intravenous (IV) fluid lines, blood access, hemodialysis, peritoneal dialysis, enteral feeding, drug vial access, and other procedures.

In some instances, the medical connection can become dislodged or disconnected in an unintended manner. For example, medical tubing of an IV set that is coupled to a catheter can become dislodged when an unintended or unexpected forces is exerted upon the catheter, which may exceed the design limitations of the catheter securement method. An unintended or unexpected force can be applied to the tubing and/or catheter when the patient moves or rolls over within a bed, or when the tubing or another portion of an intravenous set become caught on a portion of the bed, such as the railing, or when a patient is panicking, disoriented, or fidgeting to such an extent that the medical tubing is unintentionally or intentionally pulled away from the patient or away from the medical equipment coupled to the tubing.

SUMMARY

In accordance with at least some embodiments disclosed herein is the realization that unintended dislodgement or disconnection of a medical connection, such as a medical fluid line, can result in injury to a patient or a caregiver, such as by depriving the patient of a medicament, increasing the potential for infection to the patient, and exposing the caregiver to harmful medicaments.

Accordingly, aspects of the present disclosure provide a fluid connector system comprising: a first valve assembly comprising: a housing having a first end, a second end, wherein the second end is opposite to the first end, and an inner surface forming a cavity that extends through the second end toward the first end of the housing; a post having a proximal end portion and a distal end portion, wherein the distal end portion of the post extends within the cavity in a direction from the first end of the housing toward the second end of the housing; a fluid passage that extends through the first end of the housing and the post; and a compressible valve positioned in the cavity, the compressible valve having a proximal end portion and a distal end portion, wherein the proximal end portion comprises a resilient member having an inner surface forming a recess, and wherein the distal end portion comprises a head having a slit that extends through the head to the recess; a second valve assembly comprising: a body having a first end, a second end, wherein the second end is opposite to the first end, an inner surface forming a bore that extends through the second end toward the first end of the body, and a fluid passage that extends through the first end of the body to the bore; a valve plug positioned in the bore, the valve plug having a first end, a second end, and a slit that extends through the first and second ends of the valve plug; and wherein, when the first and second valve assemblies are separated from each other, the compressible valve is in a first position with a distal end of the head aligned with the second end of the housing and the distal end portion of the post positioned within the recess, and when the first and second valve assemblies are coupled together, the second end of the body is positioned within the cavity of the housing such that the compressible valve is in a second position with the head biased toward the first end of the housing and the distal end portion of the post extending through the slit of the head of the compressible valve and through the slit of the valve plug, such that the fluid passage of the first valve assembly is fluidly coupled with the fluid passage of the second valve assembly.

In some instances, the present disclosure provides methods of providing a fluid connector system, the method comprising: providing a first valve assembly comprising a housing forming a cavity having a post therein and a compressible valve extending around the post; providing a second valve assembly comprising a body forming a bore having a valve plug therein; and inserting a second end of the body into the cavity of the housing such that a head of a compressible valve is biased toward a first end of the housing; and advancing the second end of the body into the cavity of the housing such that a distal end portion of the post extends through a slit of the head of the compressible valve and through a slit of the valve plug to fluidly couple a fluid passage of the first valve assembly and a fluid passage of the second valve assembly, and a protrusion of the housing is positioned between a wall of the body and a first end of the body, wherein engagement of the protrusion against the wall resists retraction of the second valve assembly from the first valve assembly.

The present disclosure provides a valve plug for a fluid connector system, the valve plug comprising a first end, a second end, and a longitudinal axis that extends between the first and second ends of the valve plug, an inner surface forming a recess that extends through the first end of the valve plug to a floor between the first and second ends of the valve plug, a slit that extends through the second end of the valve plug and the floor; and a first portion of the inner surface forming a ridge that extends into the recess toward the longitudinal axis, and a second portion of the inner surface forming a ramp wall, the ridge comprising a first engagement surface that extends radially inward, in a direction from the first end of the valve plug toward the longitudinal axis, to an apex of the ridge, and a second engagement surface that extends radially outward from the apex and in a direction away from the longitudinal axis, and the ramp wall extending from the second engagement surface to the floor.

In some embodiments of the present disclosure, a fluid connector system comprises a first valve assembly comprising a housing having a first end, a second end, wherein the second end is opposite to the first end, and an inner surface forming a cavity that extends through the second end toward the first end of the housing, a post having a proximal end portion and a distal end portion, wherein the distal end portion of the post extends within the cavity in a direction from the first end of the housing toward the second end of the housing, and a fluid passage that extends through the first end of the housing and the post, and a second valve assembly comprising a body having a first end, a second end, wherein the second end is opposite to the first end, an inner surface forming a bore that extends through the second end toward the first end of the body, and a fluid passage that extends through the first end of the body to the bore, a valve plug positioned in the bore, the valve plug having a first end, a second end, and an inner surface forming a recess that extends through the first end of the valve plug to a floor between the first and second ends of the valve plug, a slit that extends through the second end of the valve plug and the floor, and a first portion of the inner surface forming a ridge that extends into the recess toward a longitudinal axis of the valve plug, and wherein, when the first and second valve assemblies are separated from each other, opposing inner surfaces of the valve plug forming the slit are engaged against each other to resist a fluid flow through the valve plug, and when the first and second valve assemblies are coupled together, the distal end portion of the post extends through the slit and the ridge of the valve plug, such that the fluid passage of the first valve assembly is fluidly coupled with the fluid passage of the second valve assembly, and the ridge is engaged against the post to resist movement of a fluid between the post and the ridge.

Accordingly, the present application addresses several operational challenges encountered in prior fluid connections and provides numerous improvements that enable the user to increase safety and efficacy, while more easily and precisely providing fluid connections.

Additional features and advantages of the subject technology will be set forth in the description below, and in part will be apparent from the description, or may be learned by practice of the subject technology. The advantages of the subject technology will be realized and attained by the structure particularly pointed out in the written description and embodiments hereof as well as the appended drawings.

It is to be understood that both the foregoing general description and the following detailed description are exemplary and explanatory and are intended to provide further explanation of the subject technology.

BRIEF DESCRIPTION OF THE DRAWINGS

Various features of illustrative embodiments of the inventions are described below with reference to the drawings. The illustrated embodiments are intended to illustrate, but not to limit, the inventions. The drawings contain the following figures:

FIG. 4 illustrates a cross-sectional view of the fluid connector system of FIGS. 3A and 3B, in accordance with aspects of the present disclosure.

FIG. 5 illustrates a cross-sectional view of the fluid connector system of FIG. 2, in accordance with aspects of the present disclosure.

DETAILED DESCRIPTION

In the following detailed description, numerous specific details are set forth to provide a full understanding of the subject technology. It should be understood that the subject technology may be practiced without some of these specific details. In other instances, well-known structures and techniques have not been shown in detail so as not to obscure the subject technology.

Further, while the present description sets forth specific details of various embodiments, it will be appreciated that the description is illustrative only and should not be construed in any way as limiting. Additionally, it is contemplated that although particular embodiments of the present disclosure may be disclosed or shown in the context of an IV set, such embodiments can be used in other fluid conveyance systems. Furthermore, various applications of such embodiments and modifications thereto, which may occur to those who are skilled in the art, are also encompassed by the general concepts described herein.

In accordance with some embodiments, the present application discloses various features and advantages of a fluid connector system. The fluid connector system can provide for efficient and safe maintenance of fluid connections, such as the connections used for transferring medical fluids toward or away from a patient. The fluid connector system can maintain a fluid pathway by resisting unintended disconnection when a pulling or tension force is applied to the fluid connector system, such as when a patient moves or when the medical tubing is pulled away from the patient.

The fluid connector system can also prevent injury to a patient or a caregiver by permitting disconnection or separation between portions of the connector system when a pulling or tension force exceeds a threshold. The fluid connector system can also prevent injury to a patient or a caregiver by obstructing the fluid pathway when disconnection or separation between portions of the connector system occurs. Further, the fluid connector system can provide for efficient and safe reestablishment of the fluid pathway, by permitting reassembly of portions of the system after a disconnection or separation occurs.

Figure 1:
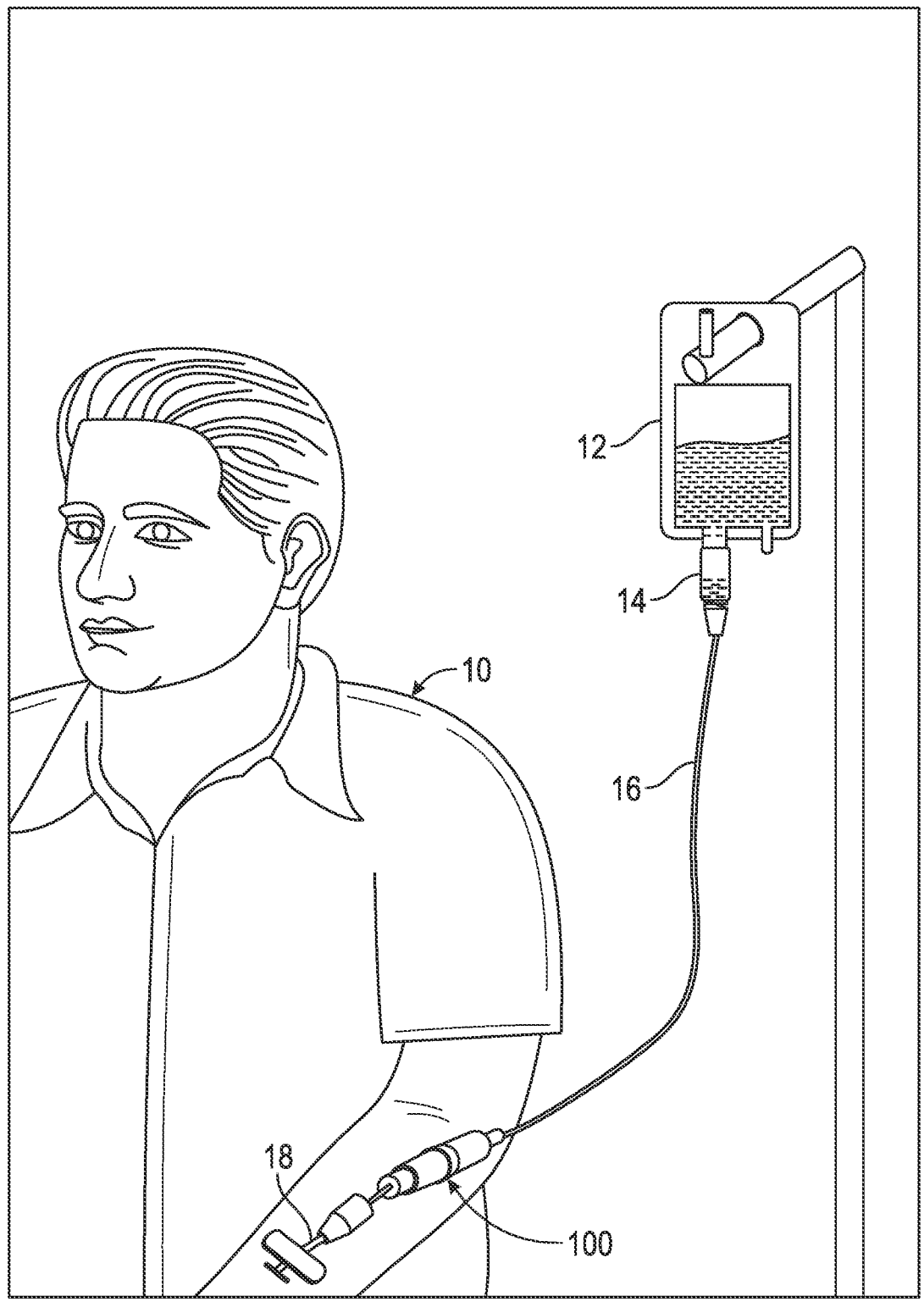
FIG. 1 illustrates a fluid connector system in use with an IV set coupled to a patient, in accordance with aspects of the present disclosure.

Referring now to the figures, FIG. 1 illustrates an example of a fluid connector system in use in accordance with aspects of the present disclosure. The connector system 100 is coupled with tubing of an IV set, which is being used to direct a fluid to a patient 10. The IV set can include a medicament bag 12, a drip chamber 14, tubing 16, and an IV catheter 18.

The connector system 100 fluidly connects the tubing 16 to the IV catheter 18. Although the connector system 100 is illustrated being coupled along a fluid pathway of an IV set, between a medicament bag 12 and a patient 10, it should be understood that the connector system 100 can be connected within other fluid pathways, such as between a patient and a IV pump or between a patient and a dialysis machine. The connector system 100 can also be connected along another portion of a fluid pathway. For example, the connector system 100 can be connected along a proximal portion of the fluid pathway, such as being connected between the tubing 16 and the medicament bag 12 or other fluid therapy device.

Figure 2:
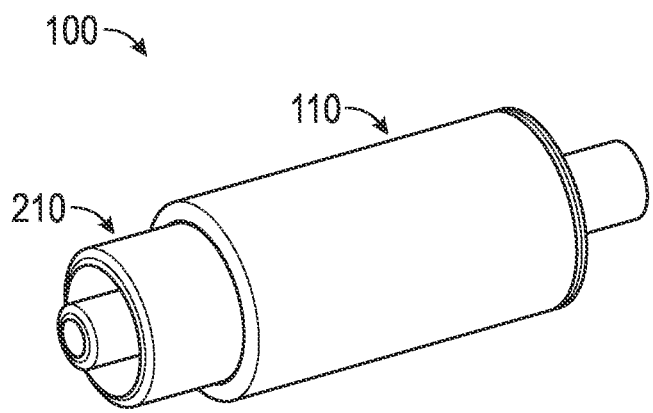
FIG. 2 illustrates a perspective view of a fluid connector system, in accordance with aspects of the present disclosure.

The connector system 100 includes a first valve assembly 110 and a second valve assembly 210, which are illustrated in FIG. 2. The first and second valve assemblies 110, 210 can be coupled together by inserting a portion of the second valve assembly 210 into the first valve assembly 110. When the first valve assembly 110 and the second valve assembly 210 coupled together, a fluid pathway is formed through the connector system 100.

Figure 3A:
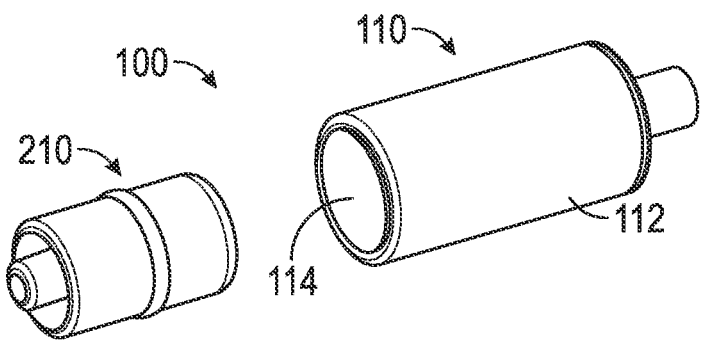
FIGS. 3A and 3B illustrate perspective views of the fluid connector system of FIG. 2, in accordance with aspects of the present disclosure.
Figure 3B:
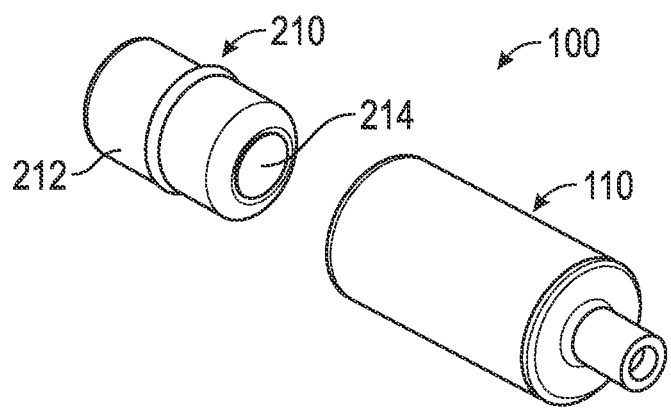

If any of the first valve assembly 110 and the second valve assembly 210 are pulled away from each other, such as when a pulling or tension force on the connector system 100 exceeds a threshold, the first valve assembly 110 and the second valve assembly 210 can separate from each other. When the first and second valve assemblies 110, 210, separate from each other, as illustrated in FIGS. 3A and 3B, the respective first and second valve assemblies 110, 210 can resist a fluid flow therethrough. In some embodiments of the present disclosure, each of the first and second valve assemblies 110, 210 can resist fluid flow by obstructing a fluid passage through their respective assemblies.

The first valve assembly 110 includes a housing 112 with an inner cavity and a compressible valve 114 positioned in the cavity. When the first valve assembly 110 is not coupled with the second valve assembly 210 or other mating connector, the compressible valve 114 is in a first position, wherein a fluid passage through the first valve assembly 110 is obstructed by the compressible valve 114 to resist fluid flow through the fluid passage of the first valve assembly 110.

When the first valve assembly 110 is coupled with the second valve assembly 210, the compressible valve 114 is moved to a second position, wherein the fluid passage through the first valve assembly 110 is unobstructed to reduce the resistance to a fluid flow through the fluid passage of the first valve assembly 110.

The second valve assembly 210 includes a body 212 with an inner bore and a valve plug 214 positioned in the bore 220. When the first valve assembly 110 is not coupled with the second valve assembly 210, a fluid passage through the second valve assembly 210 is obstructed by the valve plug 214.

When the first and second valve assemblies 110, 210 are coupled together, a portion of the first valve assembly 110 moves or biases the valve plug 214 to fluidly couple the fluid passage through the first valve assembly 110 with the fluid passage through the second valve assembly 210.

A cross-sectional view of the connector system 100 is illustrated in FIGS. 4 and 5. The first valve assembly 110 includes a housing 112 having a first end 116 and a second end 118. An inner surface of the housing 112 form a cavity 119 that at extends through the second end 118 toward the first end 116 of the housing.

The first valve assembly 110 also includes a post 120 that extends within the cavity and forms at least a portion of a fluid passage through the first valve assembly 110. The post includes a proximal end portion 122 and a distal end portion 124, where the distal end portion 124 of the post extends within the cavity in a direction from the first end 116 of the housing toward the second end 118 of the housing. In some embodiments of the present disclosure, the proximal end portion 122 of the post is coupled with the first end 116 of the housing such that the fluid passage 126 of the first valve assembly 110 extends through the first end 116 of the housing and the post 120.

The post 120 includes an inner surface forming a fluid passage 126 that extends through the proximal and distal end portions 122, 124 of the post. At the distal end portion 124 of the post, the fluid passage 126 extends through an opening at a distal end 127 of the post. In some embodiments of the present disclosure, the opening for the fluid passage is positioned at a location that is spaced apart from the distal end 127 of the post.

In some embodiments of the present disclosure, the post 120 can be configured as a needle that extends within the cavity and forms at least a portion of a fluid passage through the first valve assembly 110. The post 120 can be formed unitarily with the housing 112 or another portion of the first valve assembly 110, or the post 120 can be coupled with the housing 112 or another portion of the first valve assembly 110. In some embodiments, the post 120 is formed from a material that includes any of a polymer and/or a metal.

In some aspects of the present disclosure, the housing 112 defines a boss 128 that extends from the first end 116 of the housing in a direction away from the second end 118 of the housing. The boss 128 can include a portion of the fluid passage 126 of the first valve assembly 110. A cross-sectional width of the fluid passage 126 that extends through the boss 128 can be configured as a bond pocket such that and end of a tubing can be positioned or inserted into the fluid passage 28. In some embodiments of the present disclosure, the cross-sectional width of the fluid passage 126 that extends through the boss 128 is approximately equal to or greater than a cross-sectional width of the tubing. In some embodiments, tubing can be coupled to the first valve assembly 110 using any of an interference fit and/or creating a bond between the first valve assembly 110 and the tubing.

The compressible valve 114 is positioned in the cavity and configured to resist fluid flow through the fluid passage 126 when the compressible valve 114 is in a first position. A fluid flow through the fluid passage 126 is resisted by a portion of the compressible valve 114 positioned between the distal end 127 of the post and the second end 118 of the housing when the compressible valve 114 is in the first position.

The compressible valve 114 includes a proximal end portion 132 and a distal end portion 134. The proximal end portion 132 comprises a resilient member having an inner surface forming a recess 136. The distal end portion 134 comprises a head 138 defining a distal end 140 of the compressible valve 114. The head 138 includes a slit 139 that extends through the head 138 to the recess 136.

Although the portion of the compressible valve 114 that forms the resilient member is illustrated as a tube shaped structure having an accordion shaped wall when viewed in cross-section, the resilient member can be formed as any structure that can bias or direct the head 138 toward the second end 118 of the housing. In some embodiments of the present disclosure, the resilient member can be formed by a spring or arms that are positioned between the head 138 and any of the first or second ends 116, 118 of the housing.

When the compressible valve 114 is in the first position, the distal end 140 of the compressible valve 114 is aligned with the second end 118 of the housing. In some embodiments of the present disclosure, a common plane intersects the distal end 140 of the compressible valve 114 and the second end 118 of the housing when the compressible valve 114 is in the first position.

To resist fluid flow through the fluid passage 126, the first valve assembly 110 is also configured so that the distal end portion 124 of the post is engaged against the head 138, thereby obstructing the fluid passage 126 of the post. In some embodiments of the present disclosure, the distal most end of the post 120 is positioned within the slit 139 of the head. The head 138 can include a cavity or concave inner surface that extends from the recess 136 toward the distal end 140 of the compressible valve 114. When the compressible valve 114 is in the first position, the head 138 is engaged against the opening of the fluid passage through the post to resist fluid flow therethrough.

When the compressible valve 114 is in the first position, the head 138 of the compressible valve can also engage a protrusion 144 of the housing. The protrusion 144 extends from the inner surface of the housing 112 in a direction into the cavity. In some embodiments of the present disclosure, the protrusion 144 is positioned at the second end 118 of the housing and extends around the perimeter of the inner surface such that, when the compressible valve 114 moves toward the first position, for example, when the head 138 moves toward the second end 118 of the housing, the head 138 engages against the protrusion 144.

In use, when the head 138 moves toward the second end 118 of the housing, engagement of the head 138 against the protrusion 144 can resist movement of the head 138 in the direction from the first end 116 toward the second end 118 of the housing. Engagement of the head 138 against the protrusion 144 can also form a seal between the head 138 and the housing 112.

The first valve assembly 110 is configured to couple with the second valve assembly 210 by inserting a portion of the second valve assembly 210 through the second end 118 of the housing 112 of the first valve assembly 110. The first valve assembly 110 and the second valve assembly 210 can then be moved toward each other to fluidly couple the first and second valve assemblies 110, 210.

FIG. 4 also illustrates a cross-sectional view of the second valve assembly 210 separated from and spaced apart from the first valve assembly 110. The second valve assembly 210 includes a body 212 having a first end 216 and a second end 218. An inner surface of the body 212 form a bore 220 that extends through the second end 218 toward the first end 216 of the body.

The body 212 also includes a fluid passage 226 that extends through the first end 216 of the body to the bore 220. The valve plug 214 is positioned in the bore 220 and is configured to obstruct the fluid passage 226 when second valve assembly 210 is not coupled with the first valve assembly 110.

The valve plug 214 includes a first end 236, a second end 238, and a slit 240 that extends through the first and second ends 236, 238 of the valve plug. The second end 238 of the valve plug is aligned with the second end 218 of the body.

In some embodiments of the present disclosure, a common plane intersects the second end 238 of the valve plug and the second end 218 of the body.

In some embodiments of the present disclosure, the second end of the body 212 extends radially inward, in a direction toward the cavity. The portion of the body 212 extends radially inward can engage against the valve plug 214 and resist movement of the valve plug 214 out of the bore 220.

In some aspects of the present disclosure, the first end 216 of the body defines a male luer 242 structure that extends in a direction away from the second end 218 and forms at least portion of the fluid passage 226. In some embodiments of the present disclosure, the first end 116, 216 of any of the first and second valve assemblies 110, 210 can include any of a bond pocket, a female luer, and/or a male luer.

The body 212 forms a wall 244 that is configured to engage against a portion of the first valve assembly 110 when the first and second valve assemblies 110, 210 are coupled together. The wall 244 can be formed by a portion of the body 212 that extends away from the outer surface in a direction that is transverse, relative to a longitudinal axis A2 extending between the first and second ends 216, 218 of the body. In some embodiments of the present disclosure, the wall 244 can be formed by a portion of the outer surface of the body 212 that is convex or concave relative to an adjacent portion of the outer surface of the body 212.

The first and second valve assemblies 110, 210 can coupled together by inserting the second end 218 of the body for the second valve assembly 210 through the opening into the cavity at the second end 118 of the housing for first valve assembly 110, as illustrated in FIG. 5.

When the body 212 is inserted into the cavity and advanced toward the first end 116 of the housing, any of the second end 218 of the body and/or the second end 238 of the valve plug engages against the distal end 140 of the compressible valve. As the second valve assembly 210 is advanced toward the first end 116 of the housing, the resilient member formed by the proximal end portion 132 of the compressible valve is compressed and the head moves toward the first end 116. Movement of the head 138 toward the first end 116 of the housing causes the distal end portion 124 of the post to move through or pierce the slit 139 of the head and the slit 240 of the valve plug.

The body 212 is advanced toward the first end 116 of the housing until the protrusion 144 of the housing moves over and past the wall 244 of the body, such that the protrusion 144 is positioned between the wall 244 and the first end 216 of the body when the first and second valve assemblies 110, 210 are coupled together.

The distance between the wall 244 and the second end 218 of the body is configured to resist separation of the first and second valve assemblies 110, 210, while maintaining the fluid pathway through the first and second valve assemblies 110, 210. The resist separation and maintaining the fluid pathway, the wall 244 is spaced apart from the second end 218 of the body is by a distance D1, where the distance D2 is approximately equal to or greater than a sum of the length L1 of the slit 139 and the length L2 of the slit 240.

When the first and second valve assemblies 110, 210 are coupled together, the opening through the distal end 127 of the post is positioned between the valve plug 214 and the first end 216 of the body so that the fluid passage 126 of the first valve assembly 110 is fluidly coupled with the fluid passage 226 of the second valve assembly 210.

Figure 6:
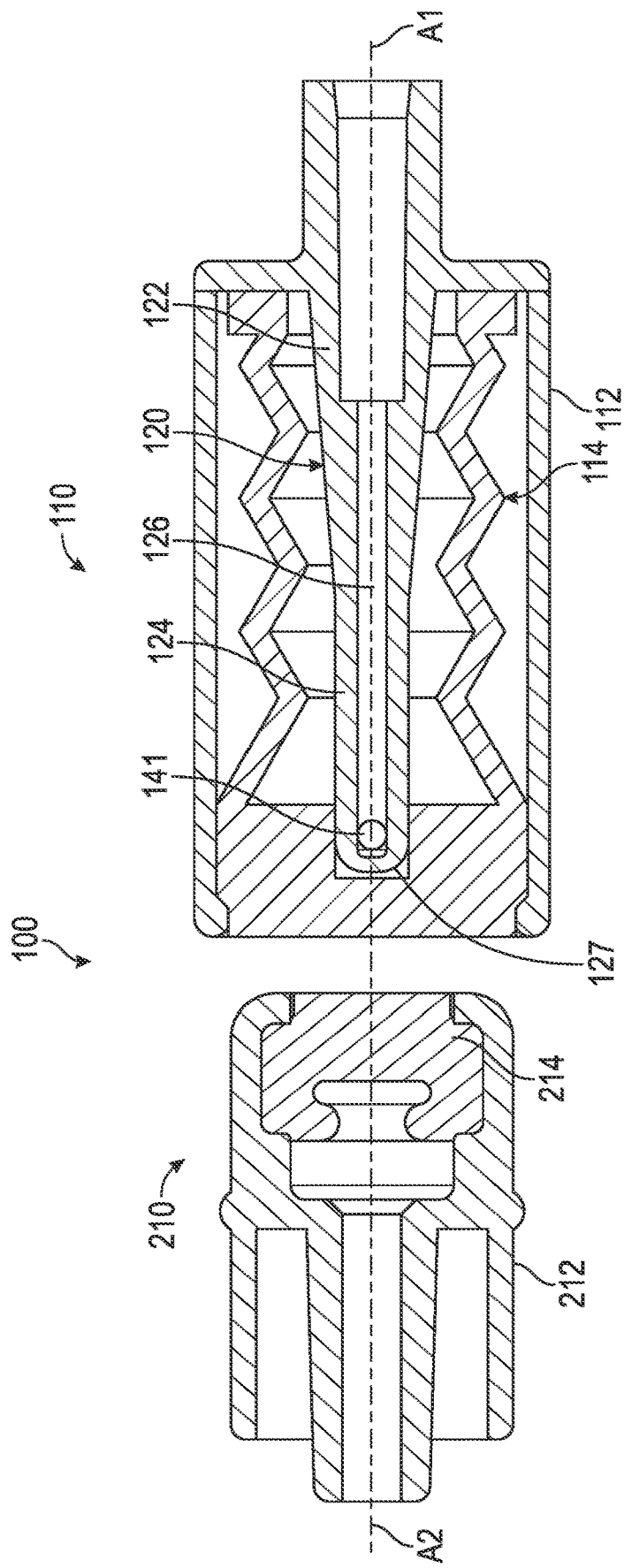
FIG. 6 illustrates a cross-sectional view of another embodiment of a fluid connector system, in accordance with aspects of the present disclosure.

In some embodiments of the present disclosure, such as the embodiment illustrated in FIG. 6, the opening 141 for the fluid passage is positioned at a location that is spaced apart from the distal end 127 of the post. The opening 141 forms a portion of the fluid passage 126 that extends in a direction that is transverse relative to the longitudinal axis A2 formed by the fluid passage 126. For example, the opening 141 at the distal end portion 124 of the post can form a portion of the fluid passage 126 that extend radially outward in a direction that extends away from the longitudinal axis A2.

The opening can be spaced apart from the distal end 127 of the post and can form a portion of the fluid passage 126 that extends in a directions that is aligned or parallel to the longitudinal axis A2. In some instances, the distal end 127 of the post has an outer surface that tapers to form a cross-sectional width that decreases in a direction from the proximal end portion 122 of the post to the distal end 127, and the opening extends through the tapered outer surface.

In some embodiments of the present disclosure, the valve plug 214 can include an inner surface forming a recess 241 that intersects the slit 240. When the first and second valve assemblies 110, 210 are coupled together, the post of the first valve assembly 110 can move through the slit 240 and the recess 241

The recess extends into the first end 236 of the valve plug, in a direction toward the second end 238 of the valve plug. The recess 241 can also include a ridge that extends from the inner surface into the recess and in a direction toward the longitudinal axis A2. The ridge can be configured to engage against the post 120 of the first valve assembly 110 to form a seal between the ridge of the valve plug 214 and the post 120. When post 120 is positioned through the valve plug 214, the ridge can resist movement of a fluid between the valve plug 214 and post 120 out of the bore 220.

Figure 7:
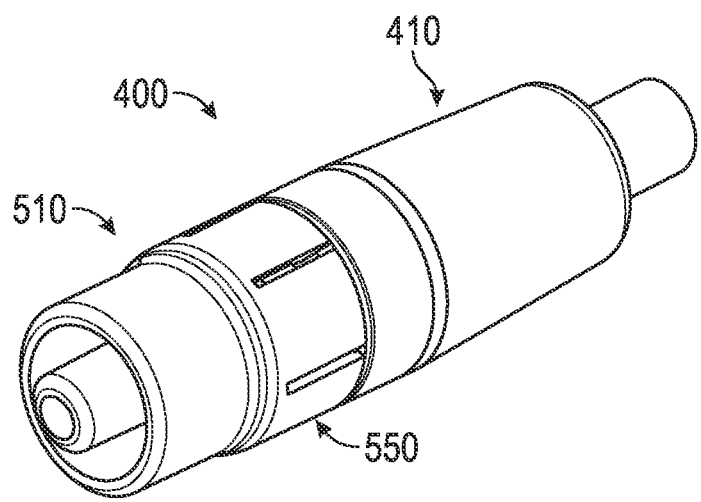
FIG. 7 illustrates a perspective view of another embodiment of a fluid connector system, in accordance with aspects of the present disclosure.

Referring to FIG. 7, an embodiment of a connector system 400 is illustrated in which a portion of the first valve assembly 410 is received into a sleeve 550 of the second valve assembly 510 when the first and second valve assemblies 410, 510 are coupled together. Features of the connector system 400 which are similar to features described with reference to other embodiments herein are not repeated herein for clarity and brevity of the present disclosure.

Figure 8A:
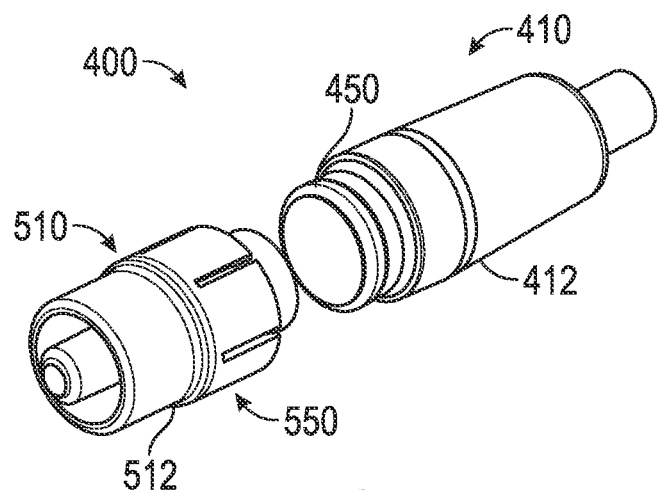
FIGS. 8A and 8B illustrate perspective views of the fluid connector system of FIG. 7, in accordance with aspects of the present disclosure.
Figure 8B:
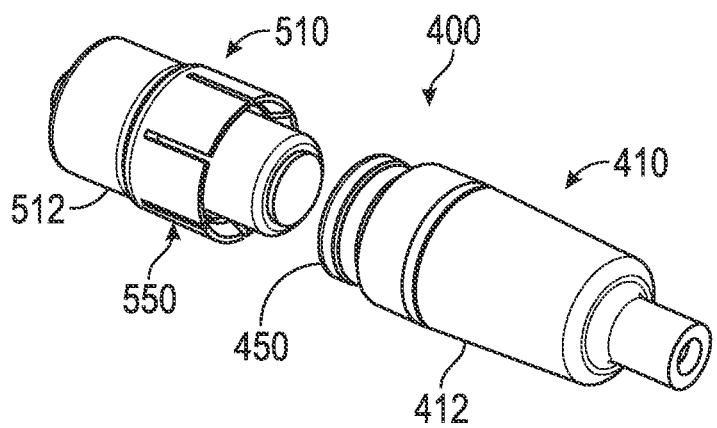

The connector system 400 is illustrated FIGS. 8A and 8B with the first valve assembly 410 disconnected or separated from the second valve assembly 510. The first valve assembly 410 includes a protrusion 460 that extends in a direction away from an outer surface of the housing 412. When the first and second valve assemblies 410, 510 are coupled together, the protrusion 460 is inserted into a space between an inner surface of the sleeve 550 and the outer surface of the body 212.

Figure 9:
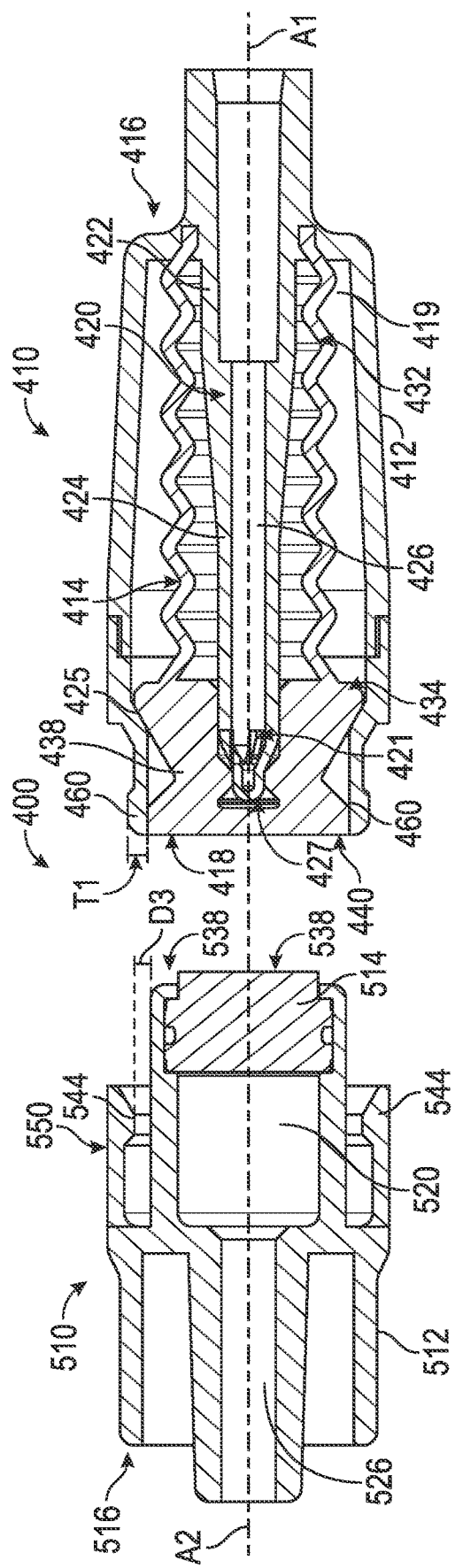
FIG. 9 illustrates a cross-sectional view of the fluid connector system of FIGS. 8A and 8B, in accordance with aspects of the present disclosure.
Figure 10:
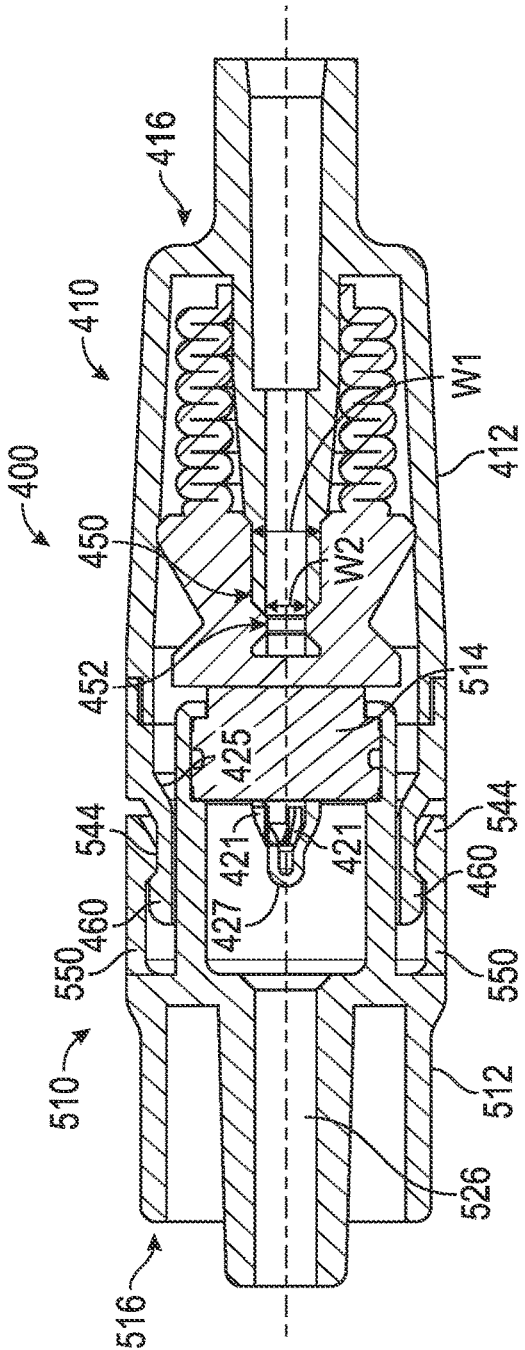
FIG. 10 illustrates a cross-sectional view of the fluid connector system of FIG. 7, in accordance with aspects of the present disclosure.

A cross-sectional view of the connector system 100 is illustrated in FIGS. 9 and 10. The first valve assembly 410 includes a housing 412 having a first end 416 and a second end 418. An inner surface of the housing 412 form a cavity that at extends through the second end 418 toward the first end 416 of the housing.

The first valve assembly 410 also includes a post 420 that extends within the cavity and forms at least a portion of a fluid passage through the first valve assembly 410. The post 420 includes a proximal end portion 422 and a distal end portion 424, where the distal end portion 424 of the post extends within the cavity in a direction from the first end 416 toward the second end 418 of the housing.

The post 420 includes an inner surface forming a fluid passage 426 that extends through the proximal and distal end portions 422, 424 of the post. At the distal end portion 424 of the post, the fluid passage 426 extends through an opening 421 that is spaced apart from a distal end 427 of the post. In some embodiments of the present disclosure, the opening 421 extends through a portion of the post having an outer surface that tapers to form a cross-sectional width that decreases in a direction away from the proximal end portion 422.

A compressible valve 414 is positioned in the cavity and configured to obstruct the fluid passage 426 when the compressible valve 414 is in a first position. The compressible valve 414 includes a proximal end portion 432 and a distal end portion 434. Like the compressible valve 114 disclosed with reference to FIGS. 4 and 5, the proximal end portion 432 comprises a resilient member and the distal end portion 434 comprises a head 438 having a slit that extends through the head 438 to a recess within resilient member.

In some embodiments of the present disclosure, the head 438 comprises an inner surface forming a portion of the recess that extends from the proximal end portion 432 toward the distal end portion 434 of the compressible valve. The recess along the head 438 can be configured so that the head engages against the post to obstruct the opening 421 when the compressible valve is in the first position.

The portion of the recess along the head 438 is formed by the inner surface having a cross-section width that is approximately equal to a cross-sectional width of the outer surface of the distal end portion 424 of the post. In some embodiments of the present disclosure, the portion of the recess along the head 438 can have a cross-sectional width that tapers to form a decreasing width in the direction from the proximal end portion 432 toward a distal end 440 of the head 438.

To engage against the post, a first portion 450 of the recess can have a cross-sectional width W1 that is approximately equal to the cross-sectional width of the outer surface of the post located between the proximal end portion 432 and the opening 421. A second portion 452 of the recess, located between the first portion 450 of the recess and a distal end 440 of the head, can have a cross-sectional width W2 that is approximately equal to the cross-sectional width of the outer surface of the post located between the opening 421 and the distal end 427 of the post.

When the compressible valve 414 is in a first position, the head 438 is positioned such that the distal end portion 424 of the post is within the recess of the head to resist a fluid flow thought the passage 426 and opening 421 of the post.

In some embodiments of the present disclosure, when the compressible valve 414 is in a first position, the inner surface of the head along the first portion 450 of the recess engages against a portion of the post between the proximal end portion 432 and the opening 421, and the inner surface of the head along the second portion 452 of the recess engages against a portion of the post between the opening 421 and the distal end 427 of the post.

When the compressible valve 414 is in the first position, the head 438 of the compressible valve can also engage a ledge 425 of the housing. The ledge 425 ends from the inner surface of the housing 412 in a direction into the cavity. In some embodiments of the present disclosure, the ledge 425 is formed by a portion of the inner surface of the housing having a cross-sectional width that tapers in a direction from the first end 416 toward the second end 418 of the housing.

As the compressible valve 414 moves toward the first position, an outer surface of the head 438 can engage against the ledge 425. In some embodiments of the present disclosure, the outer surface of the head 438 defines a cross-sectional width of the head that tapers so that the cross-sectional width decreases in a direction toward a distal end 440 of the head.

The housing 412 also includes a protrusion 460 that is configured to engage against the second valve assembly 510 when the first and second valve assemblies 410, 510 are coupled together. The protrusion 460 can be formed by a portion of the housing 412 that extends away from the outer surface in a direction that is transverse, relative to a longitudinal axis A1 extending between the first and second ends 416, 418 of the housing. In some embodiments of the present disclosure, the protrusion 460 can be formed by a portion of the outer surface of the housing 412 that is convex or concave relative to an adjacent portion of the outer surface of the housing 412.

The protrusion 460 is positioned at the second end 418 of the housing, and the ledge 425 is spaced apart from the protrusion 460 along the longitudinal axis A1. In some aspects of the present disclosure, the distal end 427 of the post is longitudinally positioned between the ledge 425 and the protrusion 460.

The protrusion 460 is configured to engage against the second valve assembly 510 to resist unintended separation of the first and second valve assemblies 410, 510 from each other. The second valve assembly 510 can include a body 512 with an inner bore and a valve plug 514 positioned in the bore 520. When the first valve assembly 410 is not coupled with the second valve assembly 510, the valve plug 514 obstructs a fluid passage through the second valve assembly 510.

In some embodiments of the present disclosure, the valve plug 514 includes a groove 515 that extends into an outer surface between the first and second ends of the valve plug. The groove 515 can extend around the circumference of the valve plug and in a direction toward the longitudinal axis A2 of the second valve assembly 510. In some aspects, the groove 515 can permit the valve plug 514 to flex or bias when the post 420 is moved through the valve plug 514.

To resist unintended separation of the first and second valve assemblies 410, 510 from each other, the second valve assembly 510 includes a sleeve 550. The sleeve extends along the outer surface of the body 512, in a direction from the first end 516 toward the second end 518 of the body. In some embodiments, the sleeve 550 extends in a direction that is parallel to a longitudinal axis A2 extending between the first and second ends 516, 518 of the body.

The sleeve 550 is spaced apart from the body 512 to permit insertion of a portion of the first valve assembly 410 therebetween. The space between the sleeve 550 and the body 512 is formed between an inner surface of the sleeve 550 and an outer surface of the body 512.

When a portion of the first valve assembly 410 is positioned between the sleeve 550 and the body 512, engagement of the sleeve 550 and the housing 412 against each other can resist unintended separation of the first and second valve assemblies 410, 510 from each other.

The portion of the sleeve 550 that engages against the housing 412 can include a wall 544. The wall 544 extends away from the inner surface of the sleeve in a direction toward the outer surface of the body 512. In some embodiments of the present disclosure, a distal end of the wall is spaced apart from the outer surface of the body 512 by a distance D3. Where the distance D3 is less that a thickness T1 of the distal end of the housing 412, the sleeve can flex or bias away from the outer surface of the body 512 when the second end 418 of the housing 412 to be inserted between the sleeve 550 and the body 512.

A cross-sectional view of the first and second valve assemblies 410, 510 coupled together is illustrated in FIG. 10. When the body 512 is inserted into the cavity of the housing 412 and advanced toward the first end 416 of the housing, any of the second end 518 of the body and/or the second end 538 of the valve plug engages against the distal end 440 of the compressible valve 414.

As the body 512 and the housing 412 are moved toward each other, the second end 418 of the housing moves into the space between the sleeve 550 and the outer surface of the body 512. The body 512 and the housing 412 are then moved further toward each other until the protrusion 460 is positioned between the wall 544 and the first end 516 of the body such that engagement of the protrusion 460 against the wall 544 resists unintended separation of the first and second valve assemblies 410, 510 from each other.

When the body 512 is inserted into the cavity of the housing 412, and advanced toward the first end 416 of the housing, the fluid passage 426 of the housing becomes fluidly coupled with the fluid passage 526 of the body when the body 512 is advanced into the housing 412 by a distance in which the opening 421 through the distal end portion of the post is positioned between the valve plug 514 and the first end 516 of the body.

In some embodiments of the present disclosure, the distal end 427 of the post is longitudinally positioned between the ledge 425 and the protrusion 460 so that, when the first and second valve assemblies 410, 510 coupled together, the opening 421 through the distal end portion of the post is positioned between the valve plug 514 and the first end 516 of the body.

When the first and second valve assemblies 410, 510 are coupled together, a fluid pathway of the connector system 400 is formed by the fluid passage 426 of the first valve assembly 410 and the fluid passage 526 of the second valve assembly 510. When the first and second valve assemblies 410, 510 are disconnected or separated from each other, the compressible valve 414 moves to an unrestrained position so that the head 438 obstructs or resist fluid flow through the post, and the valve plug 514 resists fluid flow through the fluid passage 526.

An embodiment of the valve plug 615 for the connector system is illustrated in FIGS. 11 to 15. The valve plug 615 includes features that seal or restrict a fluid pathway through the valve plug when low and high pressures are exerted on the valve. A high fluid pressure can be exerted on the valve when a post 120, 420 of a fluid coupling assembly is inserted through the valve plug 615 and a pressure is directed against the valve plug by a fluid from the post or connector system. To resist the formation of an unintended pathway between the post 120, 420 and the valve plug 615, which can result in fluid leakage therebetween, features of the valve plug 615 provide a substantially uniform sealing pressure against the post 120, 420 of the fluid coupling assembly.

The valve plug 615 includes a first end 636, a second end 638, and a slit 640 that extends through the second end 638 of the valve plug an in a direction toward the first end 636 of the valve plug. The slit 640 is formed by inner surfaces of the valve plug 615 and forms a pathway through at least a portion of the valve plug 615. The slit 640 can permit insertion of a post for a valve assembly therethrough and can close the pathway when a post is not inserted through the valve plug 615.

When the valve plug 615 is in a disconnected state, e.g., no post 120, 420 of a fluid coupling assembly extending into the valve plug, the inner surfaces of the valve plug 615 that form the slit 640 are engaged against each other to close or obstruct the pathway through the slit. When the valve plug 615 is in a connected state, e.g., a post 120, 420 of a fluid coupling assembly extending into the valve plug, at least a portion of the inner surfaces of the valve plug 615 that form the slit 640 are moved away from each other by insertion of the post therebetween, and the portion of the inner surfaces of the valve plug 615 that form the slit 640 engage against the post to resist movement of a fluid between the post and the valve plug 615.

Figure 11:
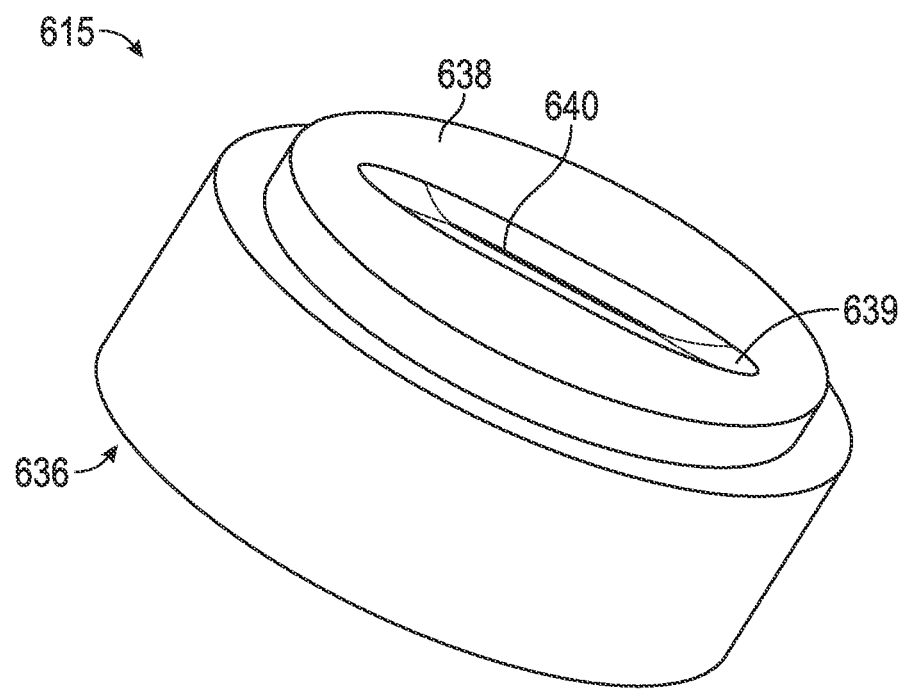
FIG. 11 illustrates a perspective view of another embodiment of a valve plug, in accordance with aspects of the present disclosure.
Figure 12:
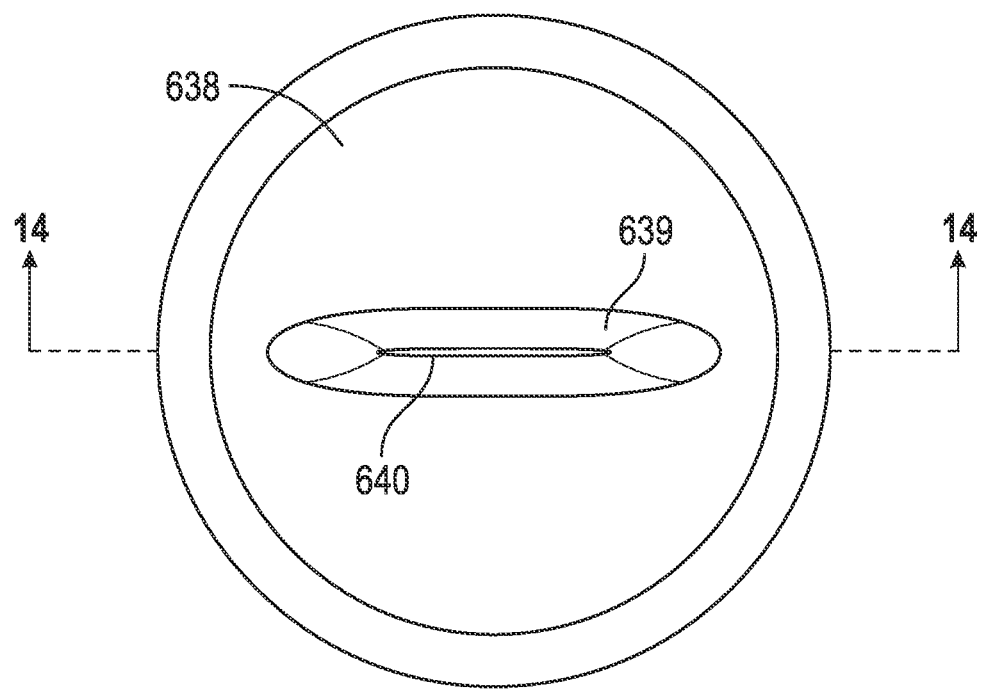
FIG. 12 illustrates a top plan view of the valve plug of FIG. 11, in accordance with aspects of the present disclosure.
Figure 14:
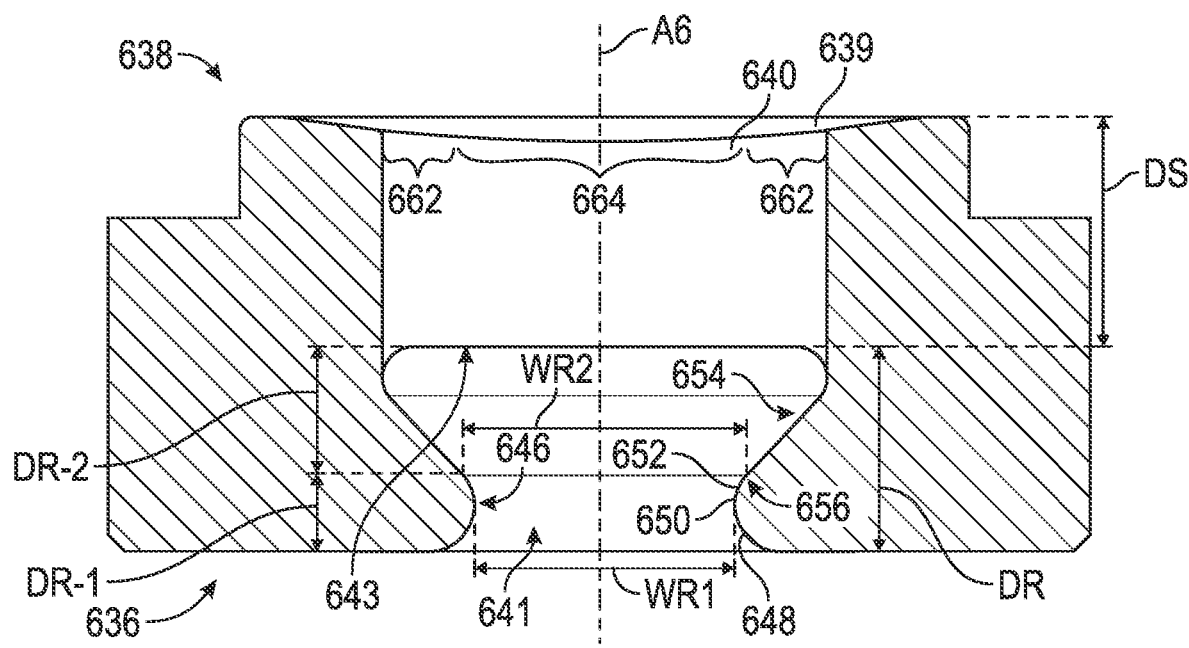
FIG. 14 illustrates a cross-sectional view of the valve plug of FIG. 12, in accordance with aspects of the present disclosure.

In some embodiments of the second end 638 of the valve plug includes a recessed or concave surface 639, illustrated in FIGS. 11, 12, and 14, that extends in a direction from the second end 638 toward the first end of the valve plug. The concave surface 639 and slit 640 are aligned relative to each other such that the slit 640 is approximately centered in the concave surface 639.

Figure 13:
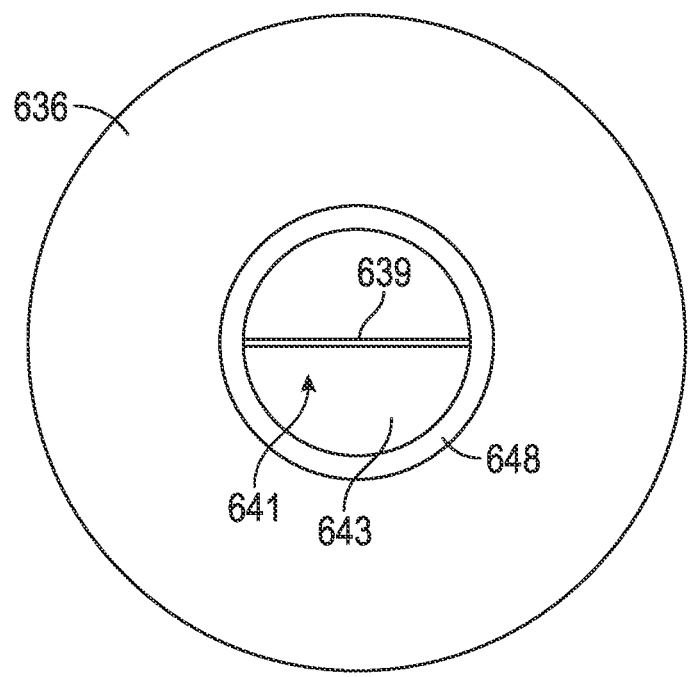
FIG. 13 illustrates a bottom plan view of the valve plug of FIG. 11, in accordance with aspects of the present disclosure.

Referring to FIGS. 13 and 14, another portion of the inner surface of the valve plug 615 can form a recess 641 that extends through the first end 636 of the valve plug to a floor 643 between the first and second ends 636, 638 of the valve plug. The slit 640 extends through the floor 643 thereby creating a pathway through the slit 640 and the recess 641, and entirely through the first and second ends 636, 638 of the valve plug.

The inner surface of the valve plug 615 also forms a ridge 646 that extends radially inward toward a longitudinal axis A6 defined between the first and second ends 636, 638 of the valve plug. The ridge 646 includes a first engagement surface 648 that extends radially inward, in a direction from the first end 636 of the valve plug toward the longitudinal axis A6, to an apex 650 of the ridge. A second engagement surface 652 of the ridge extends radially outward from the apex 650, in a direction away from the longitudinal axis A6 and toward the floor 643 of the recess.

Between the ridge 646 and the floor 643, the inner surface of the valve plug forms a ramp wall 654. The ramp wall 654 has a length that extends from a first end 656 of the ramp wall at the second engagement surface 652 of the ridge to a second end of the ramp wall at the floor 643 of the recess.

At least a portion of the length of the ramp wall 654 is oriented extending in a direction away from the longitudinal axis A6. The ramp wall 654 forms a straight conical surface between the second engagement surface 652 and the floor 643. In some embodiments of the present disclosure, the entire length of the ramp wall 654 forms a straight conical surface that extends in direction away from the longitudinal axis A6. In some embodiments, a portion of the length of the ramp wall 654 can extend in a direction that is parallel to the longitudinal axis A6 and/or in a direction away from the longitudinal axis A6. The present disclosure also contemplates embodiments in which the entire length of the ramp wall 654, or a portion thereof, forms any of a concave surface extending away from the longitudinal axis A6, and a convex surface extending toward the longitudinal axis A6.

The ridge 646 is configured to engage against a post for a valve assembly that is inserted into the recess 641 the vale plug. In some embodiments of the present disclosure, at least the apex 650 of the ridge can engage against the post to create a seal between the post and the valve plug 615 that resists movement of a fluid therebetween.

The ramp wall 654 has a perimeter that extends around or encircles the longitudinal axis A6. The perimeter of the ramp wall 654 is configured to extend entirely around the longitudinal axis of the valve plug 615, thereby forming a toroid shape around the longitudinal axis A6. In some instances, embodiments of the present disclosure, the ramp wall 654 is discontinuous along its perimeter. In some embodiments, the discontinuity of the ramp wall 654 can be formed by any of a channel, a groove, a ridge, and/or a dimple formed on the ramp wall 654.

The inner surface of the valve plug 615 defines a width of the recess 641, transverse relative to the longitudinal axis A6, that varies between the first end 636 of the valve plug and the floor 643. The recess has a first width WR1 at the apex 650 of the ridge, and the recess has a second width WR2 at the first end of the ramp wall 654 adjacent to the second engagement surface 652. The inner surface of the valve plug 615 is formed so that the smallest width of the recess 641 is at the first width WR1 at the apex 650 of the ridge, and the width at other portions of the recess is greater that the first width WR1.

The width of the recess 641, transverse relative to the longitudinal axis A6, increases and decreases between the first end 636 of the valve plug and the floor 643. Along the first engagement surface 648, the width increases from the first end 636 of the valve plug to the apex 650 of the ridge. Along the second engagement surface 652, the width of the recess decreases from the apex 650 of the ridge to the ramp wall 654. Along the ramp wall 654, the width increases in a direction toward the floor 643.

The recess 641 extends into the valve plug by a total distance DR from the first end 636 of the valve plug to the floor, where the total distance has a first portion DR-1 and a second portion DR-2. The ridge 646 extends along the first portion DR-1 of the distance of the recess, and the ramp wall 654 extends along the second portion DR-2 of the distance of the recess. The second portion DR-2 of the distance of the recess is greater than the first portion DR-1 of the distance of the recess. In some instance of the present disclosure, the total distance DR from the first end 636 of the valve plug to the floor 643 is less than a distance DS from the second end 638 of the valve plug to the floor 643.

The valve plug 615 provides a fluid pathway that is sealed when the valve plug is in a disconnected state, e.g., no post 120, 420 of a fluid coupling assembly extending into the valve plug, and the valve plug provides a substantially uniform sealing pressure when the valve plug is in a connected state, e.g., a post 120, 420 of a fluid coupling assembly extending into the valve plug. The uniform sealing pressure provided by the valve plug 615 is illustrated in FIG. 15, which shows the magnitude of pressure directed by the slit 640 and the ridge 646 against a post 120, 420 of a fluid coupling assembly, where the post 120, 420 is omitted in FIG. 15 for clarity.

The pressure directed by the ridge 646 against a post 120, 420 of a fluid coupling assembly is uniformly distributed around the entire perimeter of the ridge 646, thereby resisting movement or leakage of a fluid between the post 120, 420 and the ridge 646. The pressure P1 exerted by the ridge 646 against the post 120, 420 is uniformly distributed around the perimeter of the post 120, 420. The pressure exerted by the ridge is greatest at the apex 650 and decreases in a direction away from the apex 650, along the first and second engagement surfaces 648, 652.

The pressure P2 exerted by the slit 640 against the post 120, 420 is less at a lateral end portion 662 of the slit 640, relative to the pressure exerted by the slit 640 against the post 120, 420 a middle portion 664 of the slit. In some embodiments of the present disclosure, a distance from the apex 650 to the floor 643 of the recess is greater than a distance from the first end 636 of the valve plug to the apex 650, which provide for the pressure P2 exerted by the slit 640 against the post 120, 420 to be greatest along the second engagement surface 652 of the ridge.

Figure 15:
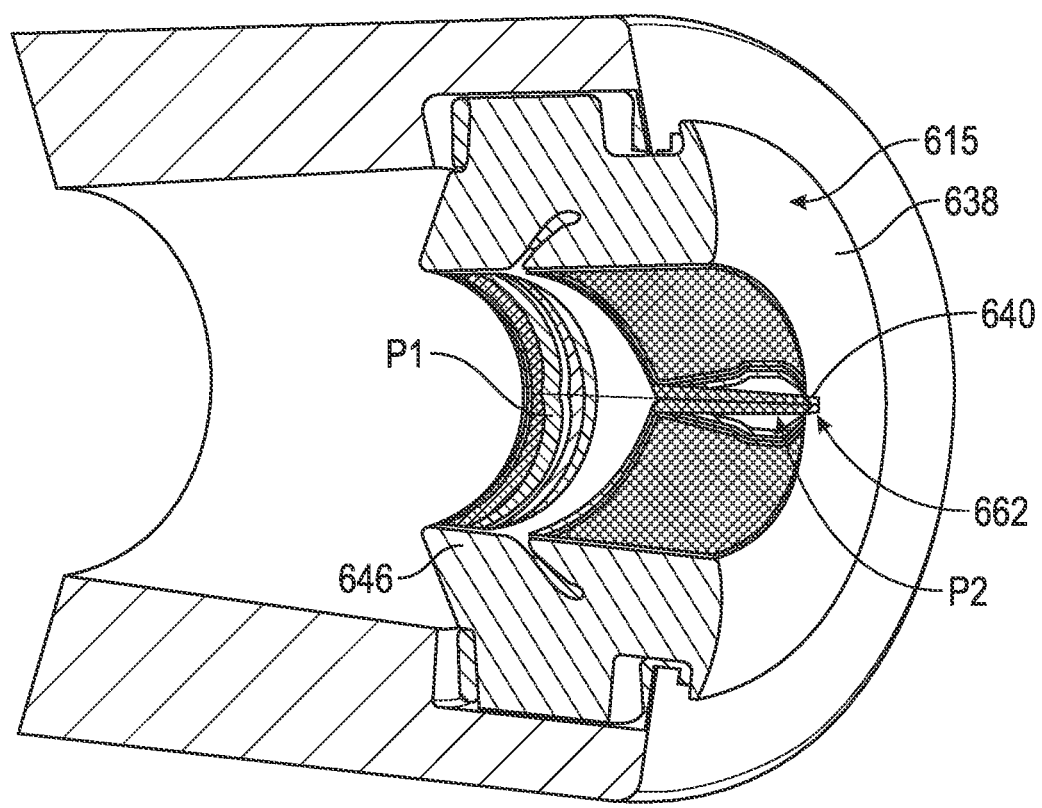
FIG. 15 illustrates a distribution of force on the valve plug of FIG. 11 during use, in accordance with aspects of the present disclosure.

When the post 120, 420 of a fluid coupling assembly is inserted into the valve plug, a portion of the valve plug forming the slit 640 can move or be deflected into the recess, as shown, for example, in FIG. 15. In some embodiments of the present disclosure, the middle portion 664 of the slit is deflected into the recess 641 and at least a portion of the floor 643 is moved into the portion of the recess along the ramp wall 654, which is identified as the second portion DR-2 of the distance of the recess in FIG. 14.

When the post 120, 420 of a fluid coupling assembly is withdrawn or otherwise removed from the valve plug 615, the valve plug is in a disconnected state in which the inner surfaces forming the slit 640 engage against each other to close the fluid pathway through the valve plug 615 and resist movement of a fluid therethrough.

In some embodiments of the present disclosure, the valve plug 615 can resist movement of a fluid through the slit 640 in the disconnected state when the fluid pressure is between approximately 1 PSI and approximately 120 PSI. In some embodiments, the valve plug 615 can resist movement of a fluid through the slit 640 in the disconnected state when the fluid pressure is approximately 60 PSI or less. In some embodiments of the present disclosure, the valve plug 615 can resist movement or leakage of a fluid between the post 120, 420 and the ridge 646 in the connected state when the fluid pressure is between approximately 1 PSI and approximately 480 PSI. In some embodiments, the valve plug 615 can resist movement or leakage of a fluid between the post 120, 420 and the ridge 646 when the fluid pressure is approximately 320 PSI or less.

It should be understood that although the present disclosure discloses the valve plug 615 as a single uniform component, the present disclosure contemplates embodiments in which the valve plug 615 is formed by two separate components, where a first component forms the first end 636, the ridge 646 and the ramp wall 654, and a second component forms the slit 640 and the second end 638. The first and second components can be assembled together or bonded together to form the valve plug 615. In some embodiments of the present disclosure, the first and second components can be positioned in a valve assembly 210, 410 such that the first and second components are spaced apart by a distance therebetween.

Illustration of Subject Technology as Clauses

The subject technology is illustrated, for example, according to various aspects described below. Various examples of aspects of the subject technology are described as numbered clauses (1, 2, 3, etc.) for convenience. These are provided as examples and do not limit the subject technology. It is noted that any of the dependent clauses may be combined in any combination, and placed into a respective independent clause, e.g., clause 1 or clause 5. The other clauses can be presented in a similar manner.

Clause 1. Accordingly, aspects of the present disclosure provide a fluid connector system comprising: a first valve assembly comprising: a housing having a first end, a second end, wherein the second end is opposite to the first end, and an inner surface forming a cavity that extends through the second end toward the first end of the housing; a post having a proximal end portion and a distal end portion, wherein the distal end portion of the post extends within the cavity in a direction from the first end of the housing toward the second end of the housing; a fluid passage that extends through the first end of the housing and the post; and a compressible valve positioned in the cavity, the compressible valve having a proximal end portion and a distal end portion, wherein the proximal end portion comprises a resilient member having an inner surface forming a recess, and wherein the distal end portion comprises a head having a slit that extends through the head to the recess; a second valve assembly comprising: a body having a first end, a second end, wherein the second end is opposite to the first end, an inner surface forming a bore that extends through the second end toward the first end of the body, and a fluid passage that extends through the first end of the body to the bore; a valve plug positioned in the bore, the valve plug having a first end, a second end, and a slit that extends through the first and second ends of the valve plug; and wherein, when the first and second valve assemblies are separated from each other, the compressible valve is in a first position with a distal end of the head aligned with the second end of the housing and the distal end portion of the post positioned within the recess, and when the first and second valve assemblies are coupled together, the second end of the body is positioned within the cavity of the housing such that the compressible valve is in a second position with the head biased toward the first end of the housing and the distal end portion of the post extending through the slit of the head of the compressible valve and through the slit of the valve plug, such that the fluid passage of the first valve assembly is fluidly coupled with the fluid passage of the second valve assembly.

Clause 2. The fluid connector system of Clause 1, wherein the housing of the first valve assembly comprises a protrusion that extends from the inner surface of the housing in a direction into the cavity.

Clause 3. The fluid connector system of Clause 2, wherein the protrusion is proximal to the second end of the housing.

Clause 4. The fluid connector system of Clause 2, wherein, when the compressible valve is in the first position, the head of the compressible valve is engaged against the protrusion.

Clause 5. The fluid connector system of Clause 2, wherein, an outer surface of the body of the second valve assembly comprises a wall that extends in a direction away from the outer surface in a direction that is transverse, relative to a longitudinal axis extending between the first and second ends of the body.

Clause 6. The fluid connector system of Clause 5, wherein, when the first and second valve assemblies are coupled together, the protrusion of the first valve assembly is positioned between the wall and the first end of the body.

Clause 7. The fluid connector system of Clause 1, wherein the fluid passage of the first valve assembly comprises an opening through a distal end of the post.

Clause 8. The fluid connector system of Clause 1, wherein the fluid passage of the first valve assembly comprises an opening spaced apart from a distal end of the post.

Clause 9. The fluid connector system of any of Clauses 1 to 8, wherein the first end of the housing comprises a bond pocket that extends into the first end of the housing in a direction toward the second end of the housing, and wherein the fluid passage of the first valve assembly extends through the bond pocket.

Clause 10. The fluid connector system of any of Clauses 1 to 9, wherein the second end of the body extends radially inward in a direction toward the cavity, and wherein, the second end of the valve plug is aligned with the second end of the body.

Clause 11. The fluid connector system of any of Clauses 1 to 10, wherein the first end of the body comprises a male luer that extends in a direction away from the second end of the body, and wherein the fluid passage of the second valve assembly extends through the male luer.

Clause 12. The fluid connector system of any of Clauses 1 to 11, wherein any of the first end of the housing and the first end of the body comprise any of a bond pocket, a female luer, and/or a male luer.

Clause 13. The fluid connector system of any of Clauses 1 to 12, wherein the inner surface of the housing comprises a ledge such that a cross-sectional width of the inner surface of the housing decreases in a direction from the first end toward the second end of the housing.

Clause 14. The fluid connector system of Clause 13, wherein the housing comprises a protrusion that extends from an outer surface of the housing in a direction away from the cavity, and wherein, the ledge is spaced apart from the protrusion along a longitudinal axis extending between the first and second ends of the housing.

Clause 15. The fluid connector system of Clause 13, wherein, when the compressible valve is in the first position, the head of the compressible valve is engaged against the ledge.

Clause 16. The fluid connector system of Clause 14, wherein the second valve assembly comprises sleeve that extends along a longitudinal axis extending between the first and second ends of the body, and in a direction toward the second end of the body, and wherein an inner surface of the sleeve is spaced apart from an outer surface of the body.

Clause 17. The fluid connector system of Clause 16, wherein, a wall extends from the inner surface of the sleeve in a direction toward the outer surface of the body.

Clause 18. The fluid connector system of Clause 17, wherein, when the first and second valve assemblies are coupled together, the protrusion of the first valve assembly is positioned between the wall and the first end of the body.

Clause 19. The fluid connector system of any of Clauses 1 to 18, wherein, when the first and second valve assemblies are coupled together, a fluid can flow from the first valve assembly to the second valve assembly, or from the second valve assembly to the first valve assembly.

Clause 20. A method of providing a fluid connector system, the method comprising: providing a first valve assembly comprising a housing forming a cavity having a post therein and a compressible valve extending around the post; providing a second valve assembly comprising a body forming a bore having a valve plug therein; and inserting a second end of the body into the cavity of the housing such that a head of a compressible valve is biased toward a first end of the housing; and advancing the second end of the body into the cavity of the housing such that a distal end portion of the post extends through a slit of the head of the compressible valve and through a slit of the valve plug to fluidly couple a fluid passage of the first valve assembly and a fluid passage of the second valve assembly, and a protrusion of the housing is positioned between a wall of the body and a first end of the body, wherein engagement of the protrusion against the wall resists retraction of the second valve assembly from the first valve assembly.

Clause 21. The method of Clause 20, further comprising rotating any of the first valve assembly or the second valve assembly relative to the other of the first valve assembly and the second valve assembly.

Clause 22. A valve plug for a fluid connector system, the valve plug comprising: a first end, a second end, and a longitudinal axis that extends between the first and second ends of the valve plug; an inner surface forming a recess that extends through the first end of the valve plug to a floor between the first and second ends of the valve plug; a slit that extends through the second end of the valve plug and the floor; and a first portion of the inner surface forming a ridge that extends into the recess toward the longitudinal axis, and a second portion of the inner surface forming a ramp wall; the ridge comprising a first engagement surface that extends radially inward, in a direction from the first end of the valve plug toward the longitudinal axis, to an apex of the ridge, and a second engagement surface that extends radially outward from the apex and in a direction away from the longitudinal axis, and the ramp wall extending from the second engagement surface to the floor.

Clause 23. The valve plug of Clause 33, wherein the ramp wall forms a straight conical surface between the second engagement surface and the floor.

Clause 24. The valve plug of Clause 23, wherein the conical surface of the ramp wall extends around the longitudinal axis of the valve plug.

Clause 25. The valve plug of Clause 23, wherein the conical surface of the ramp wall extends entirely around the longitudinal axis of the valve plug.

Clause 26. The valve plug of any of Clauses 22 to 25, wherein the ridge and the ramp wall form a toroid shape that extends around the longitudinal axis of the valve plug.

Clause 27. The valve plug of any of Clauses 22 to 26, wherein a cross-sectional width of the recess, transverse relative to the longitudinal axis, decreases along the first engagement surface from the first end of the valve plug to the apex, and increases along the second engagement surface from the apex to the ramp wall.

Clause 28. The valve plug of Clause 27, wherein the cross-sectional width of the recess increases along the ramp wall to the floor of the valve plug.

Clause 29. The valve plug of any of Clauses 22 to 28, wherein a cross-sectional width of the recess at the apex is less than a cross-sectional width of the recess along the ramp wall.

Clause 30. The valve plug of any of Clauses 22 to 29, wherein the second end of the valve plug comprises a concave surface extending into the valve plug, and the slit extends though the concave surface.

Clause 31. The valve plug of any of Clauses 22 to 30, wherein a distance from the first end of the valve plug to the floor of the recess is less than a distance from the floor of the recess to the second end of the valve plug.

Clause 32. A fluid connector system comprising: a first valve assembly comprising: a housing having a first end, a second end, wherein the second end is opposite to the first end, and an inner surface forming a cavity that extends through the second end toward the first end of the housing; a post having a proximal end portion and a distal end portion, wherein the distal end portion of the post extends within the cavity in a direction from the first end of the housing toward the second end of the housing; and a fluid passage that extends through the first end of the housing and the post; a second valve assembly comprising: a body having a first end, a second end, wherein the second end is opposite to the first end, an inner surface forming a bore that extends through the second end toward the first end of the body, and a fluid passage that extends through the first end of the body to the bore; a valve plug positioned in the bore, the valve plug having a first end, a second end, and an inner surface forming a recess that extends through the first end of the valve plug to a floor between the first and second ends of the valve plug, a slit that extends through the second end of the valve plug and the floor, and a first portion of the inner surface forming a ridge that extends into the recess toward a longitudinal axis of the valve plug; and wherein, when the first and second valve assemblies are separated from each other, opposing inner surfaces of the valve plug forming the slit are engaged against each other to resist a fluid flow through the valve plug, and when the first and second valve assemblies are coupled together, the distal end portion of the post extends through the slit and the ridge of the valve plug, such that the fluid passage of the first valve assembly is fluidly coupled with the fluid passage of the second valve assembly, and the ridge is engaged against the post to resist movement of a fluid between the post and the ridge.

Clause 33. The fluid connector system of Clause 32, wherein a second portion of the inner surface of the valve plug forms a ramp wall having a conical surface extending between the ridge and the floor.

Clause 34. The fluid connector system of Clause 33, wherein the conical surface of the ramp wall extends around the longitudinal axis of the valve plug.

Clause 35. The fluid connector system of Clause 33, wherein the conical surface of the ramp wall extends entirely around the longitudinal axis of the valve plug.

Clause 36. The fluid connector system of Clause 33, wherein a cross-sectional width of the recess, transverse relative to the longitudinal axis, decreases along a first engagement surface of the valve plug that extends from the first end of the valve plug to an apex of the ridge, and increases along a second engagement surface of the valve plug that extends from the apex to the ramp wall.

Clause 37. The fluid connector system of Clause 36, wherein the cross-sectional width of the recess increases along the ramp wall to the floor of the valve plug.

Clause 38. The fluid connector system of Clause 33, wherein the ridge and the ramp wall form a toroid shape that extends around the longitudinal axis of the valve plug.

Clause 39. The fluid connector system of Clause 33, wherein a cross-sectional width of the recess at an apex of the ridge is less than a cross-sectional width of the recess along the ramp wall.

Clause 40. The fluid connector system of any of Clauses 32 to 39, wherein the second end of the valve plug comprises a concave surface extending into the valve plug, and the slit extends though the concave surface.

Clause 41. The fluid connector system of any of Clauses 32 to 40, wherein, when the first and second valve assemblies are coupled together, a compressible valve of the first valve assembly is engaged against the second end of the valve plug.

Further Considerations

In some embodiments, any of the clauses herein may depend from any one of the independent clauses or any one of the dependent clauses. In one aspect, any of the clauses (e.g., dependent or independent clauses) may be combined with any other one or more clauses (e.g., dependent or independent clauses). In one aspect, a claim may include some or all of the words (e.g., steps, operations, means or components) recited in a clause, a sentence, a phrase or a paragraph. In one aspect, a claim may include some or all of the words recited in one or more clauses, sentences, phrases or paragraphs. In one aspect, some of the words in each of the clauses, sentences, phrases or paragraphs may be removed. In one aspect, additional words or elements may be added to a clause, a sentence, a phrase or a paragraph. In one aspect, the subject technology may be implemented without utilizing some of the components, elements, functions or operations described herein. In one aspect, the subject technology may be implemented utilizing additional components, elements, functions or operations.

The present disclosure is provided to enable any person skilled in the art to practice the various aspects described herein. The disclosure provides various examples of the subject technology, and the subject technology is not limited to these examples. Various modifications to these aspects will be readily apparent to those skilled in the art, and the generic principles defined herein may be applied to other aspects.

A reference to an element in the singular is not intended to mean "one and only one" unless specifically so stated, but rather "one or more." Unless specifically stated otherwise, the term "some" refers to one or more. Pronouns in the masculine (e.g., his) include the feminine and neuter gender (e.g., her and its) and vice versa. Headings and subheadings, if any, are used for convenience only and do not limit the invention.

The word "exemplary" is used herein to mean "serving as an example or illustration." Any aspect or design described herein as "exemplary" is not necessarily to be construed as preferred or advantageous over other aspects or designs. In one aspect, various alternative configurations and operations described herein may be considered to be at least equivalent.

A phrase such as an "aspect" does not imply that such aspect is essential to the subject technology or that such aspect applies to all configurations of the subject technology. A disclosure relating to an aspect may apply to all configurations, or one or more configurations. An aspect may provide one or more examples. A phrase such as an aspect may refer to one or more aspects and vice versa. A phrase such as an "embodiment" does not imply that such embodiment is essential to the subject technology or that such embodiment applies to all configurations of the subject technology. A disclosure relating to an embodiment may apply to all embodiments, or one or more embodiments. An embodiment may provide one or more examples. A phrase such an embodiment may refer to one or more embodiments and vice versa. A phrase such as a "configuration" does not imply that such configuration is essential to the subject technology or that such configuration applies to all configurations of the subject technology. A disclosure relating to a configuration may apply to all configurations, or one or more configurations. A configuration may provide one or more examples. A phrase such a configuration may refer to one or more configurations and vice versa.

In one aspect, unless otherwise stated, all measurements, values, ratings, positions, magnitudes, sizes, and other specifications that are set forth in this specification, including in the claims that follow, are approximate, not exact. In one aspect, they are intended to have a reasonable range that is consistent with the functions to which they relate and with what is customary in the art to which they pertain.

In one aspect, the term "coupled" or the like may refer to being directly coupled. In another aspect, the term "coupled" or the like may refer to being indirectly coupled.

Terms such as "top," "bottom," "front," "rear" and the like if used in this disclosure should be understood as referring to an arbitrary frame of reference, rather than to the ordinary gravitational frame of reference. Thus, a top surface, a bottom surface, a front surface, and a rear surface may extend upwardly, downwardly, diagonally, or horizontally in a gravitational frame of reference.

Various items may be arranged differently (e.g., arranged in a different order, or partitioned in a different way) all without departing from the scope of the subject technology. All structural and functional equivalents to the elements of the various aspects described throughout this disclosure that are known or later come to be known to those of ordinary skill in the art are expressly incorporated herein by reference and are intended to be encompassed by the claims. Moreover, nothing disclosed herein is intended to be dedicated to the public regardless of whether such disclosure is explicitly recited in the claims. No claim element is to be construed under the provisions of 35 U.S.C. § 112, sixth paragraph, unless the element is expressly recited using the phrase "means for" or, in the case of a method claim, the element is recited using the phrase "step for." Furthermore, to the extent that the term "include," "have," or the like is used, such term is intended to be inclusive in a manner similar to the term "comprise" as "comprise" is interpreted when employed as a transitional word in a claim.

The Title, Background, Summary, Brief Description of the Drawings and Abstract of the disclosure are hereby incorporated into the disclosure and are provided as illustrative examples of the disclosure, not as restrictive descriptions. It is submitted with the understanding that they will not be used to limit the scope or meaning of the claims. In addition, in the Detailed Description, it can be seen that the description provides illustrative examples and the various features are grouped together in various embodiments for the purpose of streamlining the disclosure. This method of disclosure is not to be interpreted as reflecting an intention that the claimed subject matter requires more features than are expressly recited in each claim. Rather, as the following claims reflect, inventive subject matter lies in less than all features of a single disclosed configuration or operation. The following claims are hereby incorporated into the Detailed Description, with each claim standing on its own as a separately claimed subject matter.

The claims are not intended to be limited to the aspects described herein, but is to be accorded the full scope consistent with the language claims and to encompass all legal equivalents. Notwithstanding, none of the claims are intended to embrace subject matter that fails to satisfy the requirement of 35 U.S.C. § 101, 102, or 103, nor should they be interpreted in such a way.

What is claimed is:

1. A valve plug for a fluid connector system, the valve plug comprising:
   a first end, a second end, and a longitudinal axis that extends between the first and second ends of the valve plug;
   an inner surface forming a recess that extends through the first end of the valve plug to a floor between the first and second ends of the valve plug;
   a slit that extends through the second end of the valve plug and the floor; and
   a first portion of the inner surface forming a ridge that extends into the recess toward the longitudinal axis, and a second portion of the inner surface forming a ramp wall;
   the ridge comprising a first engagement surface that extends radially inward, in a direction from the first end of the valve plug toward the longitudinal axis, to an apex of the ridge, and a second engagement surface that extends radially outward from the apex and in a direction away from the longitudinal axis, and the ramp wall extending from the second engagement surface to the floor such that a first distance from the apex to the floor is greater than a second distance from the first end of the valve plug to the apex.

2. The valve plug of claim 1, wherein the ramp wall forms a straight conical surface between the second engagement surface and the floor.

3. The valve plug of claim 2, wherein the conical surface of the ramp wall extends around the longitudinal axis of the valve plug.

4. The valve plug of claim 2, wherein the conical surface of the ramp wall extends entirely around the longitudinal axis of the valve plug.

5. The valve plug of claim 1, wherein the ridge and the ramp wall form a toroid shape that extends around the longitudinal axis of the valve plug.

6. The valve plug of claim 1, wherein a cross-sectional width of the recess, transverse relative to the longitudinal axis, decreases along the first engagement surface from the first end of the valve plug to the apex, and increases along the second engagement surface from the apex to the ramp wall.

7. The valve plug of claim 6, wherein the cross-sectional width of the recess increases along the ramp wall to the floor of the valve plug.

8. The valve plug of claim 1, wherein a cross-sectional width of the recess at the apex is less than a cross-sectional width of the recess along the ramp wall.

9. The valve plug of claim 1, wherein the second end of the valve plug comprises a concave surface extending into the valve plug, and the slit extends though the concave surface.

10. The valve plug of claim 1, wherein a distance from the first end of the valve plug to the floor of the recess is less than a distance from the floor of the recess to the second end of the valve plug.

11. A fluid connector system comprising:
    a first valve assembly comprising:
       a housing having a first end, a second end, wherein the second end is opposite to the first end, and an inner surface forming a cavity that extends through the second end toward the first end of the housing;
       a compressible valve within the cavity;
       a post having a proximal end portion and a distal end portion, wherein the distal end portion of the post extends within the cavity in a direction from the first end of the housing toward the second end of the housing; and
       a fluid passage that extends through the first end of the housing and the post;
    a second valve assembly comprising:
       a body having a first end, a second end, wherein the second end is opposite to the first end, an inner surface forming a bore that extends through the second end toward the first end of the body, and a fluid passage that extends through the first end of the body to the bore; and
       a valve plug positioned in the bore, the valve plug having a first end, a second end, and an inner surface forming a recess that extends through the first end of the valve plug to a floor between the first and second ends of the valve plug, a slit that extends through the second end of the valve plug and the floor, and a first portion of the inner surface forming a ridge that extends into the recess toward a longitudinal axis of the valve plug;
    wherein, when the first and second valve assemblies are separated from each other, opposing inner surfaces of the valve plug forming the slit are engaged against each other to resist a fluid flow through the valve plug, and when the first and second valve assemblies are coupled together, the compressible valve of the first valve assembly is engaged against the second end of the valve plug, the distal end portion of the post extends through the slit and the ridge of the valve plug, such that the fluid passage of the first valve assembly is fluidly coupled with the fluid passage of the second valve assembly, and the ridge is engaged against the post to resist movement of a fluid between the post and the ridge.

12. The fluid connector system of claim 11, wherein a second portion of the inner surface of the valve plug forms a ramp wall having a conical surface extending between the ridge and the floor.

13. The fluid connector system of claim 12, wherein the conical surface of the ramp wall extends around the longitudinal axis of the valve plug.

14. The fluid connector system of claim 12, wherein the conical surface of the ramp wall extends entirely around the longitudinal axis of the valve plug.

15. The fluid connector system of claim 12, wherein a cross-sectional width of the recess, transverse relative to the longitudinal axis, decreases along a first engagement surface of the valve plug that extends from the first end of the valve plug to an apex of the ridge, and increases along a second engagement surface of the valve plug that extends from the apex to the ramp wall.

16. The fluid connector system of claim 15, wherein the cross-sectional width of the recess increases along the ramp wall to the floor of the valve plug.

17. The fluid connector system of claim 12, wherein the ridge and the ramp wall form a toroid shape that extends around the longitudinal axis of the valve plug.

18. The fluid connector system of claim 12, wherein a cross-sectional width of the recess at an apex of the ridge is less than a cross-sectional width of the recess along the ramp wall.

19. The fluid connector system of claim 11, wherein the second end of the valve plug comprises a concave surface extending into the valve plug, and the slit extends though the concave surface.

* * * * *